(12) United States Patent
Wilkinson et al.

(10) Patent No.: US 11,166,767 B2
(45) Date of Patent: Nov. 9, 2021

(54) ALIGNMENT PRECISION

(71) Applicant: Smith & Nephew, Inc., Memphis, TN (US)

(72) Inventors: Zachary Christopher Wilkinson, Germantown, TN (US); Ryan Lloyd Landon, Olive Branch, MS (US); Brian William McKinnon, Arlington, TN (US)

(73) Assignee: Smith & Nephew, Inc., Memphis, TN (US)

( * ) Notice: Subject to any disclaimer, the term of this patent is extended or adjusted under 35 U.S.C. 154(b) by 54 days.

(21) Appl. No.: 16/819,808

(22) Filed: Mar. 16, 2020

(65) Prior Publication Data
US 2020/0214771 A1 Jul. 9, 2020

Related U.S. Application Data

(60) Division of application No. 16/298,722, filed on Mar. 11, 2019, now abandoned, which is a continuation of (Continued)

(51) Int. Cl.
*A61B 34/20* (2016.01)
*A61B 17/15* (2006.01)
(Continued)

(52) U.S. Cl.
CPC ............ *A61B 34/20* (2016.02); *A61B 17/155* (2013.01); *A61B 17/157* (2013.01);
(Continued)

(58) Field of Classification Search
None
See application file for complete search history.

(56) References Cited

U.S. PATENT DOCUMENTS

| 5,408,409 | A | 4/1995 | Glassman et al. |
| 5,871,018 | A | 2/1999 | Delp et al. |

(Continued)

FOREIGN PATENT DOCUMENTS

| EP | 1523951 A2 | 4/2005 |
| EP | 2233099 A2 | 9/2010 |

(Continued)

OTHER PUBLICATIONS

Australian Examination Report No. 1 for AU2015288038 dated Jun. 15, 2019.
(Continued)

*Primary Examiner* — Edward Park
(74) *Attorney, Agent, or Firm* — Troutman Pepper Hamilton Sanders LLP

(57) ABSTRACT

Alignment precision technology, in which a system accesses image data of a bone to which a reference marker array is fixed. The system generates a three-dimensional representation of the bone and the reference markers, defines a coordinate system for the three-dimensional representation, and determines locations of the reference markers relative to the coordinate system. The system accesses intra-operative image data that includes the bone and a mobile marker array that is attached to an instrument used in a surgical procedure. The system co-registers the intra-operative image data with the three-dimensional representation by matching the reference markers included in the intra-operative image data to the locations of the reference markers. The system determines locations of the mobile markers in the co-registered image and determines a three-dimensional spatial position and orientation of the instrument relative to the bone.

20 Claims, 15 Drawing Sheets

Related U.S. Application Data application No. 16/110,297, filed on Aug. 23, 2018, now Pat. No. 10,226,301, which is a continuation of application No. 15/102,705, filed as application No. PCT/US2015/039351 on Jul. 7, 2015, now Pat. No. 10,080,616.

(60) Provisional application No. 62/021,551, filed on Jul. 7, 2014.

(51) Int. Cl.
*A61B 17/17* (2006.01)
*A61B 34/00* (2016.01)
*A61B 90/00* (2016.01)
*A61B 34/10* (2016.01)

(52) U.S. Cl.
CPC .......... *A61B 17/1764* (2013.01); *A61B 34/00* (2016.02); *A61B 2034/102* (2016.02); *A61B 2034/107* (2016.02); *A61B 2034/2055* (2016.02); *A61B 2034/256* (2016.02); *A61B 2090/0818* (2016.02); *A61B 2090/363* (2016.02); *A61B 2090/364* (2016.02); *A61B 2090/3966* (2016.02); *A61B 2090/3983* (2016.02)

(56) References Cited

U.S. PATENT DOCUMENTS

| | | |
|---|---|---|
| 6,205,411 B1 | 3/2001 | DiGioia, III et al. |
| 8,989,844 B2 | 3/2015 | Cinquin et al. |
| 9,726,476 B2 | 8/2017 | Ramamurthy et al. |
| 2002/0107522 A1 | 8/2002 | Picard et al. |
| 2004/0002642 A1 | 1/2004 | Dekel et al. |
| 2005/0021037 A1 | 1/2005 | McCombs et al. |
| 2005/0215879 A1 | 9/2005 | Chuanggui |
| 2007/0073306 A1 | 3/2007 | Lakin et al. |
| 2007/0233121 A1 | 10/2007 | Carson et al. |
| 2011/0257653 A1 | 10/2011 | Hughes et al. |
| 2012/0041446 A1 | 2/2012 | Wong et al. |
| 2013/0060146 A1 | 3/2013 | Yang et al. |
| 2013/0211232 A1 | 8/2013 | Murphy et al. |
| 2015/0178910 A1 | 6/2015 | Lin |
| 2015/0245878 A1* | 9/2015 | Jaramaz ................. A61B 17/15 606/87 |
| 2016/0331474 A1* | 11/2016 | Lacal ..................... G16H 40/63 |
| 2020/0030034 A1* | 1/2020 | Kontaxis ................ A61B 34/10 |

FOREIGN PATENT DOCUMENTS

| | | |
|---|---|---|
| JP | 2009273521 A | 11/2009 |
| JP | 2011172920 A | 9/2011 |
| JP | 2017524445 A | 8/2017 |
| WO | 2013182224 A1 | 12/2013 |

OTHER PUBLICATIONS

Chao et al. "Simulation and Animation of Musculosketal Joint System" (Nov. 1, 1993) J. Biomechanical Engineering 115(4B): 562-568.

Delp et al. "An Interactive Graphics-Based Model of the Lower Extremity to Study Orthopaedic Surgical Procedures" (Aug. 1990) IEE Transactions on Biomedical Engineering 37(8): 757-767.

DiGioia et al. "An Integrated Approach to Medical Robotics and Computer Assisted Surgery in Orthopaedics" (1995) Carnegie Mellon University 106-111.

DiGioia et al. "HipNav: Pre-operative Planning and Intra-operative Navigational Guidance for Acetabular Implant Placement in Total Hip Replacement Surgery" (Nov. 1995) Proceedings of CAOS '96 1-8.

Dillman et al. "Haptic Devices in Medical Applications" (Jun. 23, 1999) Institute for Process Control and Robotics, 1st International Workshop, Paris, France, pp. 12-22.

European Office Action for EP 15819544.6 dated Dec. 9, 2019.

Freysinger et al. "A Passive-Marker-Based Optical System for Computer-Aided Surgery in Otorhinolaryngology: Development and First Clinical Experiences" (Feb. 2002) The Laryngoscope 112(2):409.

Harris et al. "Experiences with Robotic Systems for Knee Surgery" (Mar. 19-22, 1997) Springer-Verlag, London, UK 757-766.

International Search Report and Written Opinion for PCT/US2015/039351 dated Oct. 20, 2015, 8 pages.

Japanese Office Action for JP2019-206256 dated Dec. 24, 2020.

O'Toole III et al. "Towards More Capable and Less Invasive Robotic Surgery in Orthopaedics" (1995) Computer Vision, Virtual Reality and Robotics in Medicine 905: 123-130.

Partial European Search Report for EP 15819544 dated Jun. 2, 2018.

Supplementary European Search Report for Application No. EP15819544 dated Jun. 15, 2018.

Taylor et al. "An Image-Directed Robotic System for Precise Orthopaedic Surgery" (Jun. 1994) IEE Transactions on Robotics and Automation 10 (3): 261-275.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

* cited by examiner

ALIGNMENT PRECISION

CROSS-REFERENCE TO RELATED APPLICATIONS

This application is a divisional of U.S. patent application Ser. No. 16/298,722, filed on Mar. 11, 2019, which is a continuation of U.S. patent application Ser. No. 16/110,297, filed on Aug. 23, 2018, now U.S. Pat. No. 10,226,301 issued Mar. 12, 2019, which is a continuation of U.S. patent application Ser. No. 15/102,705, filed on Jun. 8, 2016, now U.S. Pat. No. 10,080,616 issued Sep. 25, 2018, which is a U.S. National Stage filing under 35 U.S.C. § 371 of International Application No. PCT/US2015/039351, filed on Jul. 7, 2015, which claims priority under 35 USC § 119(e) to U.S. Provisional Patent Application Ser. No. 61/021,551, filed on Jul. 7, 2014, and entitled "ALIGNMENT PRECISION", each of which is hereby incorporated herein by reference in its entirety.

FIELD

This disclosure relates to alignment precision.

BACKGROUND

Computer Assisted Surgery (CAS) tools have been developed using optical motion capture to convert three-dimensional (3D) locations of passive reflective fiducial markers into the 3D pose of surgical instruments relative to user-selected anatomic landmark points. CAS may be used as a quantitative intra-operative measurement system to assess alignment performance. CAS systems, however, were not designed for rigorous analysis required to validate intra-operative performance. For example, CAS read-outs have been commonly limited to 1 mm and 0.5-degree increments of precision, and absolute accuracy to anatomic landmarks has been difficult to validate. Also, CAS alignment was limited by the operator's ability to consistently identify anatomic landmark points. CAS anatomic landmarks have been limited to those that could be safely and quickly accessed physically on live patients. CAS systems were not primarily intended as research tools, but as tools to assist in a clinical procedure. The level of precision of CAS systems may be useful for surgeons making informed intra-operative decisions, but may not be sufficient to distinguish subtle differences between alignment methods.

SUMMARY

In one aspect, a system comprises at least one processor and at least one computer-readable medium coupled to the at least one processor having stored thereon instructions which, when executed by the at least one processor, causes the at least one processor to perform operations. The operations include accessing first image data of at least a portion of a bone to which a reference fiducial marker array is fixed in advance of a surgical procedure. The reference fiducial marker array includes at least three reference fiducial markers and the first image data is captured using a first imaging modality that is configured to image the reference fiducial markers and three-dimensional anatomic landmark data for the portion of the bone. The operations also include generating a three-dimensional representation of the portion of the bone and the reference fiducial markers based on the first image data, defining a coordinate system for the three-dimensional representation of the portion of the bone, and determining locations of the reference fiducial markers relative to the defined coordinate system. The operations further include accessing intra-operative image data that includes the portion of the bone to which to the reference fiducial marker array is fixed and a mobile fiducial marker array that is attached to an instrument used in the surgical procedure on the portion of the bone. The mobile fiducial marker array includes at least three mobile fiducial markers and the intra-operative image data is captured using a second imaging modality that is different than the first imaging modality and that is configured to image the reference fiducial markers and the mobile fiducial markers. In addition, the operations include co-registering the intra-operative image data with the three-dimensional representation of the portion of the bone by matching the reference fiducial markers included in the intra-operative image data to the determined locations of the reference fiducial markers relative to the defined coordinate system. The operations also include determining locations of the mobile fiducial markers in the co-registered intra-operative image data and three-dimensional representation of the portion of the bone and determining a three-dimensional spatial position and orientation of the instrument relative to the portion of the bone based on the determined locations of the mobile fiducial markers. The operations further include comparing the three-dimensional spatial position and orientation of the instrument relative to the portion of the bone with a designed alignment of the instrument to the portion of the bone and, based on comparison results, determining an indication of precision of alignment of the instrument in the surgical procedure on the portion of the bone relative to the designed alignment of the instrument to the portion of the bone. The operations also include providing output based on the determined indication of precision of alignment of the instrument in the surgical procedure relative to the designed alignment of the instrument.

Implementations may include one or more of the following features. For example, the operations may include accessing computed tomography (CT) image data of the portion of the bone and the reference fiducial markers and accessing intra-operative motion capture data that includes the portion of the bone to which to the reference fiducial marker array is fixed and the mobile fiducial marker array that is attached to the instrument used in the surgical procedure on the portion of the bone. In addition, the operations may include generating a three-dimensional solid that includes the portion of the bone and the reference fiducial marker array.

In some implementations, the operations may include accessing data defining three-dimensional spatial position and orientation of the instrument relative to the mobile fiducial markers determined using a computer-aided-design (CAD) model of the instrument with the mobile fiducial marker array attached. In these implementations, the operations may include determining the three-dimensional spatial position and orientation of the instrument relative to the portion of the bone by mapping the three-dimensional spatial position and orientation of the instrument relative to the mobile fiducial markers to the determined locations of the mobile fiducial markers.

Also, the operations may include accessing data defining three-dimensional spatial position and orientation of the instrument relative to the mobile fiducial markers determined using a coordinate measurement machine (CMM) evaluation of the instrument with the mobile fiducial marker array attached. The operations further may include determining the three-dimensional spatial position and orientation of the instrument relative to the portion of the bone by mapping the three-dimensional spatial position and orientation of the instrument relative to the mobile fiducial markers to the determined locations of the mobile fiducial markers.

In some examples, the operations may include accessing CMM data for the reference fiducial marker array and validating the determined locations of the reference fiducial markers using the accessed CMM data for the reference fiducial marker array. In these examples, the operations may include accessing CMM data for the mobile fiducial marker array and validating the determined locations of the mobile fiducial markers using the accessed CMM data for the mobile fiducial marker array.

In some implementations, the reference fiducial markers and the mobile fiducial markers may be radio-opaque, infrared reflective spherical markers. In these implementations, the reference fiducial marker array may include at least five reference spherical markers and the mobile fiducial marker array may include at least five mobile spherical markers. Also, in these implementations, the operations may include determining centers of the reference spherical markers and determining locations of the reference fiducial markers as the determined centers of the reference spherical markers. Further, in these implementations, the operations may include determining centers of the mobile spherical markers and determining locations of the mobile fiducial markers as the determined centers of the mobile spherical markers.

In some examples, the operations may include identifying the reference spherical markers, regression fitting each of the identified reference spherical markers with an ideal sphere shape, and determining locations of the reference spherical markers using the regression-fitted reference spherical markers. In these examples, the operations may include identifying the mobile spherical markers, regression fitting each of the identified mobile spherical markers with an ideal sphere shape, and determining locations of the mobile spherical markers using the regression-fitted reference spherical markers.

In some implementations, the operations may include identifying a measurement for cartilage related to the portion of the bone and adjusting the three-dimensional representation and the coordinate system to account for the identified measurement for cartilage related to the portion of the bone. In these implementations, the operations may include accessing magnetic resonance imaging (MRI) of the portion of the bone and determining a measurement of the cartilage based on the MRI of the portion of the bone.

In some examples, the instrument used in the surgical procedure may be a cutting block used in total knee arthroplasty (TKA). In these examples, the mobile fiducial marker array may be attached to the cutting block through the cutting slot of the cutting block and at least one other portion of the cutting block. Also, in these examples, the mobile fiducial marker array may be attached to the cutting block through the cutting slot of the cutting block and at least one pin hole of the cutting block. Further, in these examples, the mobile fiducial marker array may be attached to the cutting block through the cutting slot using a surgical blade designed to be inserted through the cutting slot and one or more shims that rigidly support the surgical blade in the cutting slot.

In addition, the operations may include accessing data descriptive of post-operative validation of cuts made during the surgical procedure and validating the determined indication of precision of alignment based on the accessed data descriptive of post-operative validation of cuts made during the surgical procedure.

In some implementations, the operations may include aggregating the determined indication of precision of alignment of the instrument in the surgical procedure relative to the designed alignment of the instrument with similar data determined from other similar surgical procedures. In these implementations, the operations may include performing statistical analysis of the aggregated data, determining a representation of general alignment precision in surgical procedures included in the aggregated data based on the statistical analysis of the aggregated data, and providing output indicating the determined representation of general alignment precision.

In another aspect, a method includes accessing first image data of at least a portion of a bone to which a reference fiducial marker array is fixed in advance of a surgical procedure. The reference fiducial marker array includes at least three reference fiducial markers and the first image data is captured using a first imaging modality that is configured to image the reference fiducial markers and three-dimensional anatomic landmark data for the portion of the bone. The method also includes generating a three-dimensional representation of the portion of the bone and the reference fiducial markers based on the first image data, defining a coordinate system for the three-dimensional representation of the portion of the bone, and determining locations of the reference fiducial markers relative to the defined coordinate system. The method further includes accessing intra-operative image data that includes the portion of the bone to which to the reference fiducial marker array is fixed and a mobile fiducial marker array that is attached to an instrument used in the surgical procedure on the portion of the bone. The mobile fiducial marker array includes at least three mobile fiducial markers and the intra-operative image data is captured using a second imaging modality that is different than the first imaging modality and that is configured to image the reference fiducial markers and the mobile fiducial markers. In addition, the method includes co-registering the intra-operative image data with the three-dimensional representation of the portion of the bone by matching the reference fiducial markers included in the intra-operative image data to the determined locations of the reference fiducial markers relative to the defined coordinate system. The method also includes determining locations of the mobile fiducial markers in the co-registered intra-operative image data and three-dimensional representation of the portion of the bone and determining a three-dimensional spatial position and orientation of the instrument relative to the portion of the bone based on the determined locations of the mobile fiducial markers. The method further includes comparing the three-dimensional spatial position and orientation of the instrument relative to the portion of the bone with a designed alignment of the instrument to the portion of the bone and, based on comparison results, determining an indication of precision of alignment of the instrument in the surgical procedure on the portion of the bone relative to the designed alignment of the instrument to the portion of the bone. The method includes providing output based on the determined indication of precision of alignment of the instrument in the surgical procedure relative to the designed alignment of the instrument.

In yet another aspect, at least one computer-readable storage medium encoded with executable instructions that, when executed by at least one processor, cause the at least one processor to perform operations. The operations include accessing first image data of at least a portion of a bone to which a reference fiducial marker array is fixed in advance of a surgical procedure. The reference fiducial marker array includes at least three reference fiducial markers and the first image data is captured using a first imaging modality that is configured to image the reference fiducial markers and three-dimensional anatomic landmark data for the portion of the bone. The operations also include generating a three-dimensional representation of the portion of the bone and the reference fiducial markers based on the first image data, defining a coordinate system for the three-dimensional representation of the portion of the bone, and determining locations of the reference fiducial markers relative to the defined coordinate system. The operations further include accessing intra-operative image data that includes the portion of the bone to which to the reference fiducial marker array is fixed and a mobile fiducial marker array that is attached to an instrument used in the surgical procedure on the portion of the bone. The mobile fiducial marker array includes at least three mobile fiducial markers and the intra-operative image data is captured using a second imaging modality that is different than the first imaging modality and that is configured to image the reference fiducial markers and the mobile fiducial markers. In addition, the operations include co-registering the intra-operative image data with the three-dimensional representation of the portion of the bone by matching the reference fiducial markers included in the intra-operative image data to the determined locations of the reference fiducial markers relative to the defined coordinate system. The operations also include determining locations of the mobile fiducial markers in the co-registered intra-operative image data and three-dimensional representation of the portion of the bone and determining a three-dimensional spatial position and orientation of the instrument relative to the portion of the bone based on the determined locations of the mobile fiducial markers. The operations further include comparing the three-dimensional spatial position and orientation of the instrument relative to the portion of the bone with a designed alignment of the instrument to the portion of the bone and, based on comparison results, determining an indication of precision of alignment of the instrument in the surgical procedure on the portion of the bone relative to the designed alignment of the instrument to the portion of the bone. The operations also include providing output based on the determined indication of precision of alignment of the instrument in the surgical procedure relative to the designed alignment of the instrument.

In yet another aspect, a method includes accessing an MRI image of at least a portion of a cadaver patient's leg that includes a knee of the cadaver patient and determining cartilage thickness for the knee of the cadaver patient based on the accessed MRI image. The method also includes accessing a CT image of at least a portion of the cadaver patient's leg that includes CT imaging of at least a portion of a femur to which a reference fiducial marker array is fixed in advance of a TKA procedure and CT imaging of at least a portion of a tibia. The reference fiducial marker array includes at least three reference fiducial markers that are captured in CT imaging and motion capture imaging. The method further includes defining, on the accessed CT image and accounting for the determined cartilage thickness, a first coordinate system for the femur and a second coordinate system for the tibia and generating a processed CT image by calculating a three-dimensional transformation between the CT image on which the first coordinate system for the femur and the second coordinate system for the tibia have been defined and a pattern of the reference fiducial marker array as measured by the CT image. In addition, the method includes accessing intra-operative motion capture data of at least a portion of the cadaver patient's leg that includes motion capture imaging of at least a portion of the femur to which the reference fiducial marker array is fixed and motion capture imaging of at least a portion of the tibia. The intra-operative motion capture data is captured during the TKA procedure on the cadaver patient's leg and includes motion capture imaging of a mobile fiducial marker array that is attached to a cutting block used in the TKA procedure on the cadaver patient's leg. The mobile fiducial marker array includes at least three mobile fiducial markers that are captured in motion capture imaging. The method also includes co-registering the intra-operative motion capture data with the processed CT image by regression fitting the reference fiducial markers included in the intra-operative motion capture data to the reference fiducial markers included in the processed CT image. The method further includes generating a processed motion capture image by calculating a three-dimensional transformation between the co-registered intra-operative motion capture data and processed CT image and a pattern of the mobile fiducial marker array as measured by the intra-operative motion capture data. And, the method includes accessing a first CAD model of the mobile fiducial marker array and co-registering the first CAD model of the mobile fiducial marker array with the processed motion capture image by regression fitting the mobile fiducial markers included in the first CAD model of the mobile fiducial marker array to the mobile fiducial markers included in the processed motion capture image. The method includes accessing a second CAD model that represents alignment of cutting block relative to the mobile fiducial marker array based on the mobile fiducial marker array being attached to the cutting block and generating an alignment image that represents alignment of the cutting block to the femur during the TKA procedure by calculating a three-dimensional transformation between the co-registered first CAD model of the mobile fiducial marker array and processed motion capture image and the second CAD model that represents alignment of cutting block relative to the mobile fiducial marker array. The method includes accessing a design for the TKA procedure that represents a designed alignment of the cutting block to the femur in the TKA procedure, comparing the alignment image that represents alignment of the cutting block to the femur during the TKA procedure with the design for the TKA procedure, and, based on comparison results, determining an indication of precision of alignment of the cutting block to the femur during the TKA procedure relative to the designed alignment of the cutting block to the femur in the TKA procedure. In addition, the method includes providing output based on the determined indication of precision of alignment of the cutting block to the femur during the TKA procedure relative to the designed alignment of the cutting block to the femur in the TKA procedure.

The details of one or more implementations are set forth in the accompanying drawings and the description, below. Other potential features of the disclosure will be apparent from the description and drawings, and from the claims.

DETAILED DESCRIPTION

Figure 1:
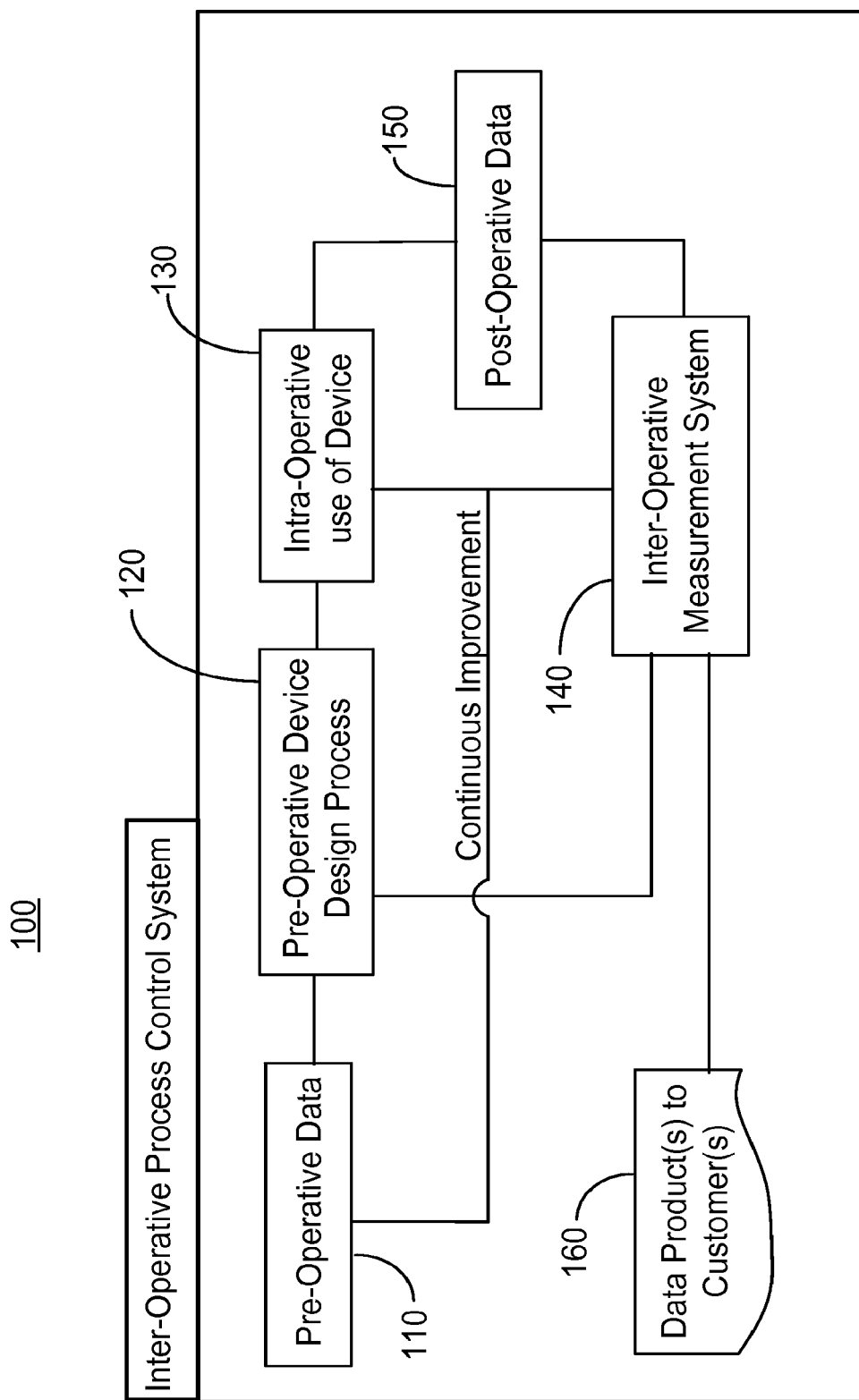
FIG. 1 is a diagram of example inter-operative process control.

Techniques are described for a system of combined high-precision imaging methods used to compare intra-operative alignment performance of total knee arthroplasty (TKA) instrumentation and techniques to pre-operatively determine alignment targets. These imaging methods acquire and process three-dimensional (3D) data of two types: pre-operative anatomic landmark data and intra-operative motion data. The former are used to establish the pre-operative alignment axes of the subject bone, and the latter establish the 3D spatial position and orientation (e.g., pose) of the subject instrument during use relative to the pre-operative alignment. Each imaging method may be non-destructively validated to pre-operative Coordinate Measurement Machine (CMM) gauge data for each test setup. The CMM data may be obtained by contact measurement or non-contact scanning. The system of the two imaging methods also may be destructively validated by comparing intra-operative and post-operative measurements of the TKA resection surfaces for each test setup.

In some implementations, this type of analysis may be challenging because few tools can simultaneously acquire both landmark and motion data. Further, a high level of precision and accuracy may be required to detect small performance differences. A single method, such as a Computer Aided Surgery (CAS) machine, which intra-operatively captures both anatomic landmarks and 3D pose data, may be used. Although CAS streamlines data acquisition, CAS may have insufficient precision and accuracy for validation testing. To improve precision and accuracy, in some examples, two, different modalities of high precision imaging may be used and co-registered to assess alignment performance. For instance, a system may use multi-modality fiducial marker arrays to co-register two specialized high-precision measurement methods. This system may involve Computed Tomography (CT) imaging for pre-operative anatomic landmark data and optical motion capture (e.g., Pro-Reflex motion capture technology provided by Qualisys AB) for 3D intra-operative instrument pose data. ProReflex is a registered trademark of Qualisys AB.

Using the techniques described throughout this disclosure, precision of a patient matched design process for TKA procedures may be validated and improved. In some implementations, the techniques described throughout this disclosure may be used in a cadaver study to validate and improve precision of the patient matched design process. In these implementations, many cadavers may be selected that have similar anatomic features at the knee joint. Then, for each cadaver, a surgical team performs a patient matched process to assess alignment precision in TKA procedures.

In the patient matched process to assess alignment precision in TKA procedures, the surgical team uses the patient matched design process to generate an implant design for the cadaver. Next, the surgical team assembles a bone rig with a reference fiducial marker array to the cadaver's bone (e.g., femur and/or tibia) and performs pre-operative imaging (e.g., MRI, CT, etc.) to generate a representation of the cadaver's bone relative to the reference fiducial marker array prior to the TKA procedure.

After the pre-operative imaging, the surgical team transports the cadaver to a surgical center and performs the TKA procedure on the cadaver while capturing motion capture imaging of the TKA procedure. The motion capture imaging captures the reference fiducial marker array and a mobile fiducial marker array that is attached to an instrument (e.g., cutting block) used in the TKA procedure. The motion capture imaging is co-registered with the pre-operative imaging using the reference fiducial marker array and, using a known alignment of the mobile fiducial marker array to the instrument, an alignment of the instrument to the bone during the TKA procedure is determined.

Then, the determined alignment of the instrument to the bone during the TKA procedure is compared to a designed alignment included in the implant design for the cadaver. The comparison provides a measure of how precisely the actual alignment meets the designed alignment. Because many cadavers were selected for the testing, the precision of the patient matched design process may be validated using statistical analysis. In addition, the surgical team may make recommendations on how to improve the patient matched design process and identify places that introduce error in alignment.

FIG. 1 illustrates an example of inter-operative process control 100. In the example process control 100, a system accesses pre-operative data 110. The pre-operative data may include image data of a bone or bone segment (e.g., CT image data, MRI image data, and/or other types of image data). The system performs a pre-operative device design process 120 based on the accessed pre-operative data. For example, the system may develop a patient-specific instrument design based on the accessed pre-operative data. In this example, the system may develop a patient-specific implant and a patient-specific cutting block that is adapted to the specific anatomy of the patient's bone. In other examples, the system uses the accessed pre-operative data to select, from a library of available designs, an instrument design that best matches the patient's anatomy.

In addition, the system monitors intra-operative use of device 130 using an inter-operative measurement system 140. For instance, the system monitors surgical placement of the designed device during a surgical procedure. The system may use motion capture data to monitor the pose of the designed device during the surgical procedure. The system may focus on the final placement of the designed device to determine the final alignment of the designed device.

The system also may access post-operative data 150 related to the accuracy and precision of the surgical procedure. The post-operative data 150 may include non-destructive validation measurements using imaging technology on the final resection cuts and/or implant placement. The post-operative data 150 also may include destructive validation measurements using physical measurement techniques (e.g., caliper measurements) on the final resection cuts and/or implant placement. The destructive validation measurements may be used when the surgical procedure is performed on a cadaver for the purpose of researching alignment precision of the alignment technique used in designing the device and performing the surgical procedure.

The inter-operative measurement system 140 uses pre-operative design data from the pre-operative device design process 120 and the post-operative data 150 to assess alignment precision during the surgical procedure. For example, the inter-operative measurement system 140 compares the pre-operative design and the post-operative data 150 to determine how closely the actual alignment of the designed device in the surgical procedure matched the designed alignment. The inter-operative measurement system 140 may use any of the techniques described throughout this disclosure to assess alignment precision (e.g., the process 400 described below with respect to FIG. 4).

The inter-operative measurement system 140 uses the results of the precision analysis, as well as other available data, to continuously improve all aspects of the surgical procedure. For example, the output of the inter-operative measurement system 140 may be used to improve the pre-operative data 110 captured, improve the pre-operative device design process 120, and/or improve the intra-operative use of device 130. In this example, the inter-operative measurement system 140 may monitor data over a large number of research procedures, identify factors that impact alignment performance, and use the identified factors to improve alignment in the overall process.

The inter-operative measurement system 140 may produce and output data product(s) to customer(s) 160. The data product(s) to customer(s) 160 may include accuracy precision in alignment for a single procedure and/or statistical analysis of a large number of procedures that indicate general alignment precision of a specific alignment process. The statistical analysis may include F and/or T tests that quantitatively indicate the alignment performance over a large number of sample procedures.

Figure 2:
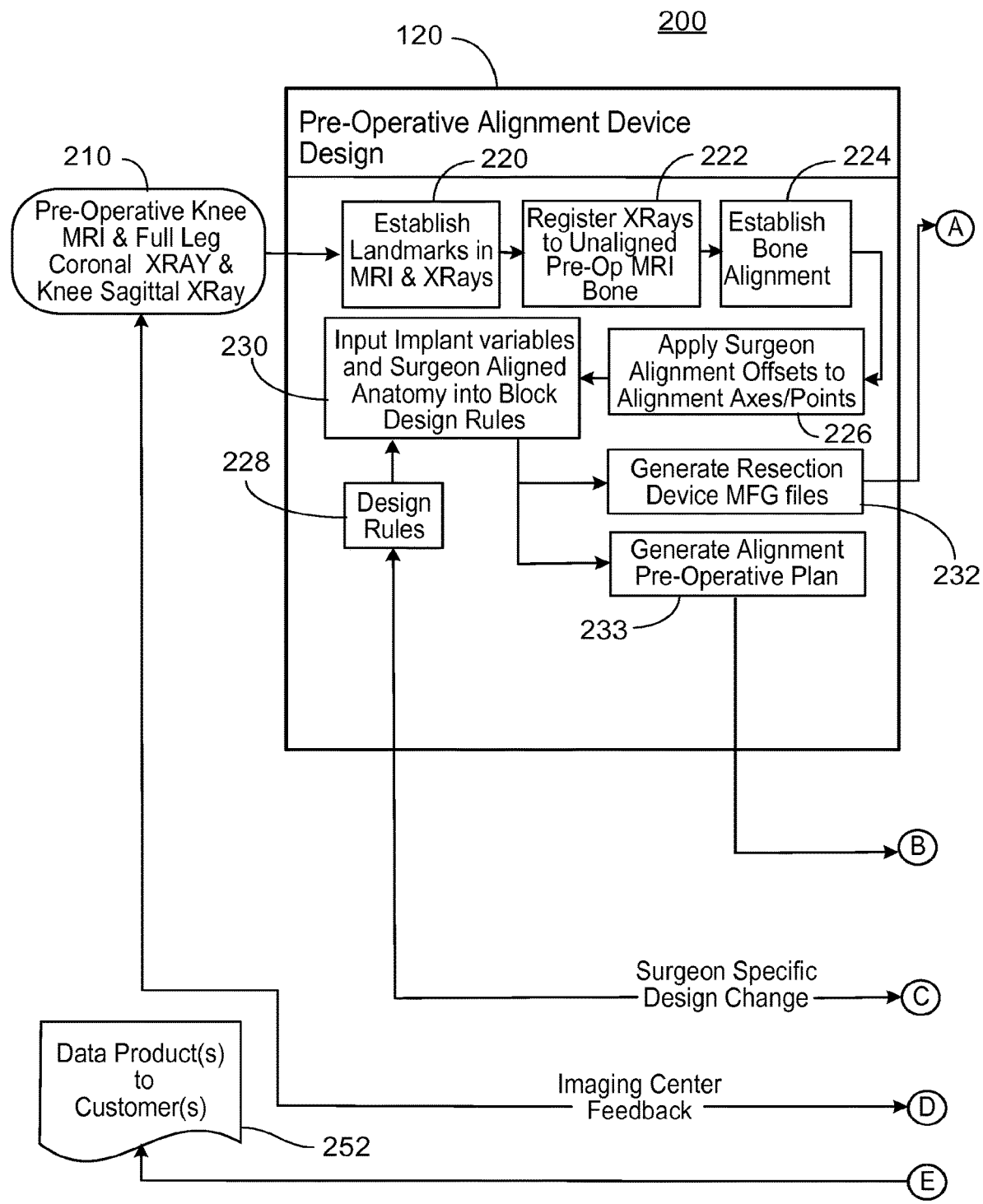
FIG. 2 is a diagram of example inter-operative alignment process control.
Figure 2:
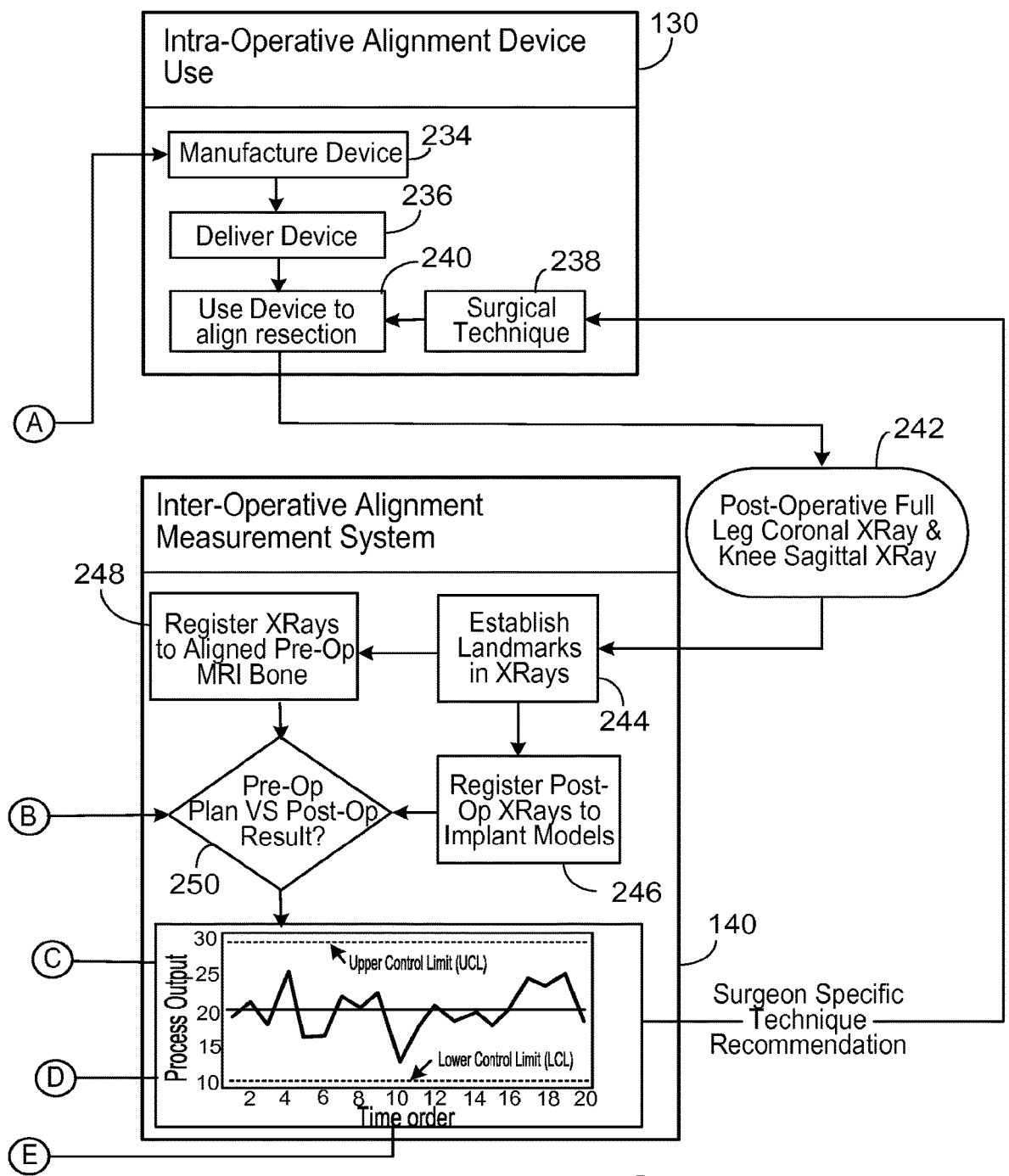

FIG. 2 illustrates an example of inter-operative alignment process control 200. The inter-operative alignment process control 200 is similar to the inter-operative process control 100, but provides additional details. In the example alignment process control 200, a system accesses pre-operative data 210. The pre-operative data may include pre-operative knee MRI and full leg coronal XRay and knee sagittal XRay.

The inter-operative alignment process control 200 shows additional operations performed in the pre-operative device design process 120. As shown, the system establishes landmarks in MRI and XRays 220, registers XRays to unaligned pre-op MRI bone 222, and establishes bone alignment 224. The system then applies surgeon alignment offsets to alignment axes/points 226 and accesses design rules 228 that are continuously improved by the inter-operative measurement system 140. The system inputs implant variables and surgeon aligned anatomy into the accessed block design rules 230, generates resection device manufacturing (MFG) files 232, and generates an alignment pre-operative plan 233.

The generated resection device MFG files 232 are used to implement intra-operative use of device 130. As part of the intra-operative use of device 130, the system manufactures the device 234 and causes the delivery of the manufactured device 236 for surgery. A surgeon applies a surgical technique 238 with the manufactured device and uses the device to align resection 240 in the surgical procedure.

After the surgical procedure, the system obtains post-operative data 242. The post-operative data 242 may include full leg coronal XRay and knee sagittal XRay.

The inter-operative measurement system 140 receives the alignment pre-operative plan 233 and the post-operative data 242 for comparison. The system establishes landmarks in XRays 244, uses the established landmarks to register post-operative XRays to implant models 246, and uses the established landmarks to register XRays to aligned pre-operative MRI bone 248. The system 140 then uses the registered post-operative XRays to implant models and the registered XRays to the aligned pre-operative MRI bone to compare pre-operative plan versus post-operative result 250. The comparison of the pre-operative plan versus post-operative result 250 results in data that indicates alignment precision in the surgical procedure. The data may indicate alignment precision at each resection cut and/or at various points of the aligned device. In addition, the system 140 may perform statistical analysis on a large number of test cases as described above with respect to FIG. 1. The system 140 may use the results of the comparison to continuously improve all aspects of the alignment design and process.

The system 140 provides and outputs data product(s) to customer(s) 252 based on the comparison. The system 140 may use techniques similar to those discussed above with respect to FIG. 1 to provide and output data product(s) to customer(s) 252. Although the discussion in FIGS. 1 and 2 focus on alignment process controls, the techniques described in FIGS. 1 and 2 (and throughout) may be applied to other process controls.

Figure 3:
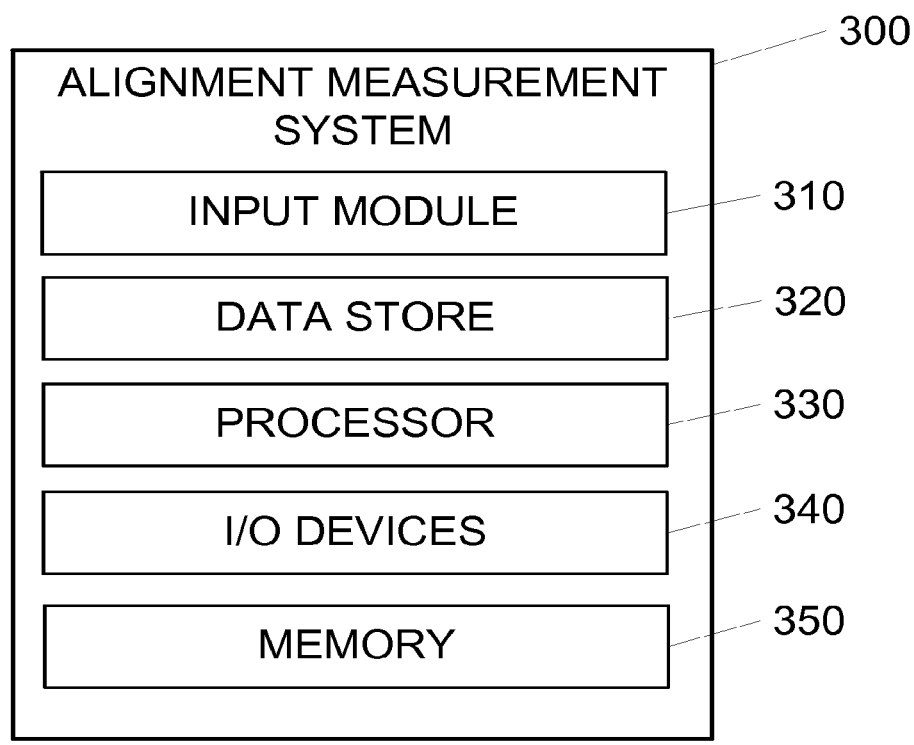
FIGS. 3 and 14 are diagrams of example systems.

FIG. 3 illustrates an example alignment measurement system 300, which may be used as the system referenced above with respect to FIGS. 1 and 2. The system 300 includes an input module 310, a data store 320, one or more processors 330, one or more I/O (Input/Output) devices 340, and memory 350. The input module 320 may be used to input any type of information used in alignment measurement and process control. For example, the input module 310 may be used to receive bone data and images of bone segments both pre- and post-operative. In some implementations, data from the input module 310 is stored in the data store 320. The data included in the data store 320 may include, for example, any type of alignment or process control related data (e.g., bone images, three-dimensional models of bones, parameters related to instrument designs, etc.).

In some examples, the data store 320 may be a relational database that logically organizes data into a series of database tables. Each database table in the data store 320 may arrange data in a series of columns (where each column represents an attribute of the data stored in the database) and rows (where each row represents attribute values). In some implementations, the data store 320 may be an object-oriented database that logically or physically organizes data into a series of objects. Each object may be associated with a series of attribute values. In some examples, the data store 320 may be a type of database management system that is not necessarily a relational or object-oriented database. For example, a series of XML (Extensible Mark-up Language) files or documents may be used, where each XML file or document includes attributes and attribute values. Data included in the data store 320 may be identified by a unique identifier such that data related to a particular process may be retrieved from the data store 320.

The processor 330 may be a processor suitable for the execution of a computer program such as a general or special purpose microprocessor, and any one or more processors of any kind of digital computer. In some implementations, the system 300 includes more than one processor 330. The processor 330 may receive instructions and data from the memory 350. The memory 350 may store instructions and data corresponding to any or all of the components of the system 300. The memory 350 may include read-only memory, random-access memory, or both.

The I/O devices 340 are configured to provide input to and output from the system 300. For example, the I/O devices 340 may include a mouse, a keyboard, a stylus, a camera, or any other device that allows the input of data. The I/O devices 340 may also include a display, a printer, or any other device that outputs data.

Figure 4:
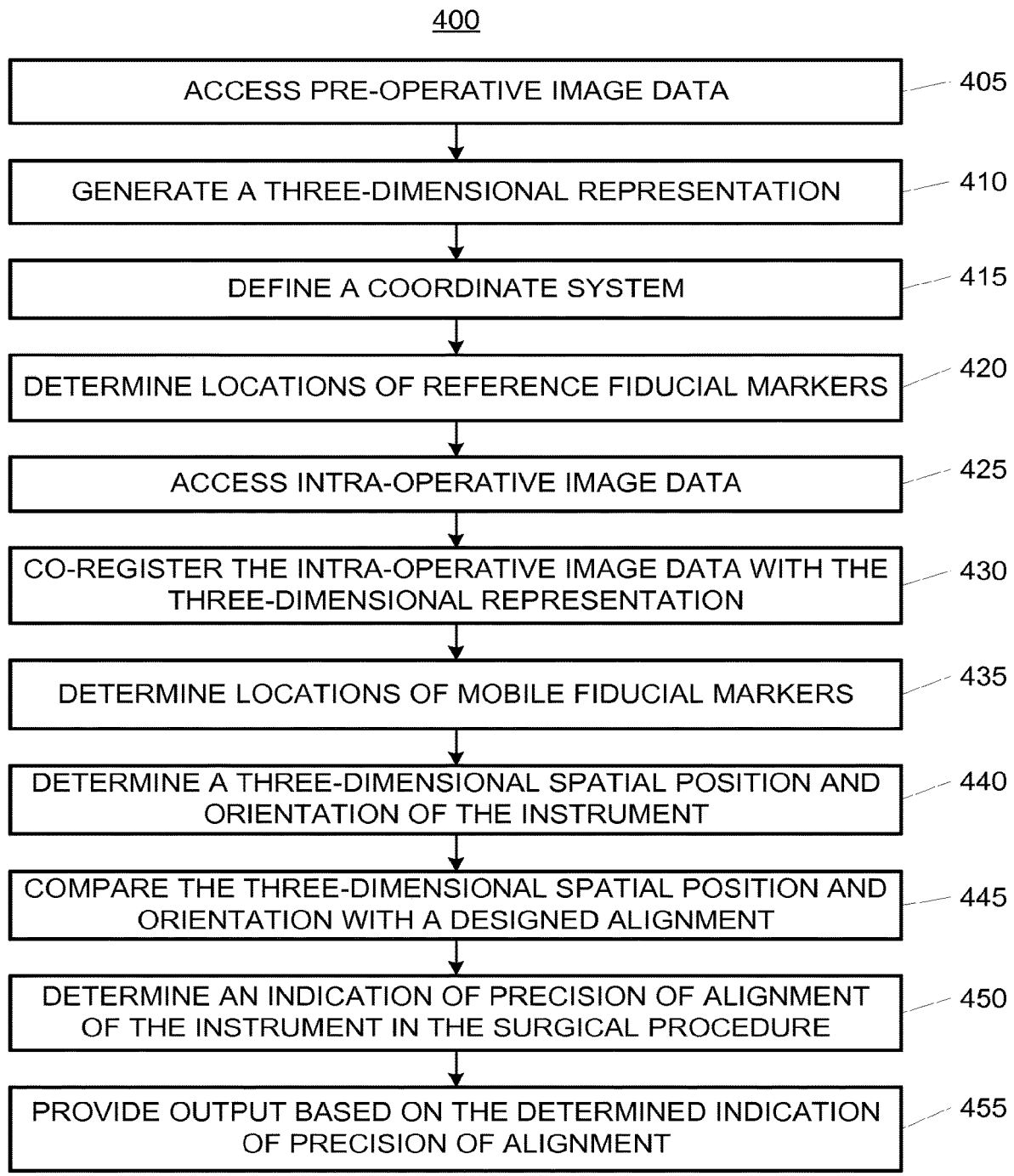
FIGS. 4, 12, and 13 are flowcharts of example processes.

FIG. 4 illustrates a process 400 used in alignment precision measurement. The operations of the process 400 are described generally as being performed by the system 300. In some implementations, operations of the process 400 may be performed by one or more processors included in one or more electronic devices.

In some implementations, the process 400 is performed on cadaver patients to assess the alignment precision in patient-matched design processes used in performing a surgical procedure. In these implementations, the results and output provided by the process 400 are used to validate the precision of the patient-matched design processes on the cadaver patients and improve the patient-matched design processes used in future live patients, where assembling the bone rig to enable image registration in multiple imaging modalities would not be performed.

The system 300 accessing pre-operative image data of at least a portion of a bone to which a reference fiducial marker array is fixed (405). The reference fiducial marker array may include at least three reference fiducial markers and the pre-operative image data may be captured using a first imaging modality that is configured to image the reference fiducial markers and three-dimensional anatomic landmark data for the portion of the bone. For instance, the system 300 accesses pre-operative computed tomography (CT) image data of the portion of the bone and the reference fiducial markers. The system 300 may control the CT imaging system to capture images of the portion of the bone and the reference fiducial markers and access the CT images as the pre-operative image data. Other types of imaging technologies (e.g., three-dimensional imaging technologies that are capable of capturing a three-dimensional image of bone) may be used.

In implementations in which the techniques described throughout this disclosure are used in knee implants (e.g., TKA), the system 300 accesses pre-operative image data of at least a portion of a femur and/or a tibia. For instance, the system 300 may access pre-operative image data of an entire femur or tibia, or may access pre-operative image data of a portion of the femur or tibia located at the knee joint (e.g., the portion of the femur or tibia that receives an implant during TKA). In addition, the techniques described throughout this disclosure may be applied to other types of implant procedures (e.g., hip replacement, shoulder replacement, etc.). For other types of implant procedures, the system 300 may access pre-operative image data of a portion of the bone that receives the implant, such as a portion of the bone located at a joint associated with the implant procedure.

Figure 5:
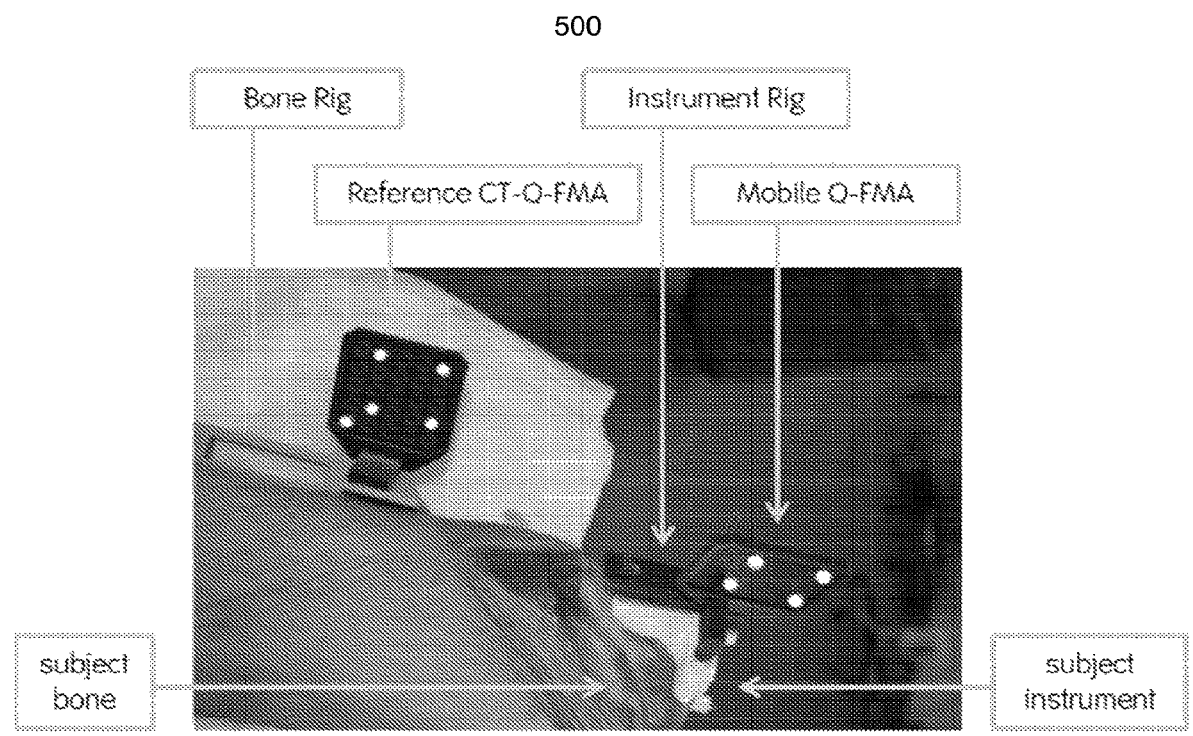
FIG. 5 is a diagram of an example assembly of a subject bone, a subject instrument, a bone rig, an instrument rig, a reference fiducial marker array, and a mobile fiducial marker array.

FIG. 5 illustrates an example assembly of a subject bone, a subject instrument, a bone rig, an instrument rig, a reference fiducial marker array, and a mobile fiducial marker array. As shown in FIG. 5, multiple spherical fiducial markers are rigidly attached to a small rectangular frame to form a fiducial marker array. Due to the properties of the spherical markers (e.g., radio-opaque, infrared reflective), the fiducial marker array is measureable by both CT imaging and optical motion capture (e.g., ProReflex motion capture technology provided by Qualisys AB). One array is rigidly attached to the subject bone during pre-operative imaging and remains attached during intra-operative testing in order to serve as a fixed datum reference between the CT image of subject bone and the motion capture measured subject instrument 3D pose. Therefore, this array may be referred to as the reference CT-Qualisys-Fiducial Marker Array (CT-Q-FMA). A second array is rigidly attached to the subject instrument during intra-operative testing, thereby enabling measurement of the 3D pose of the subject instrument with respect to the reference CT-Q-FMA. This second array may be referred to as the mobile Q-FMA.

The reference CT-Q-FMA frame may be composed of CT and MR compatible Objet Digital ABS Polyjet Photopolymer RGD515/535 and manufactured on an Objet Connex 500 3D Printer. The spherical multi-modality markers used in the reference CT-Q-FMA may be constructed from a CT and MR compatible, radio-opaque plastic coated with an infrared reflective paint. The manufacturing of the reference CT-Q-FMA may not affect measurement precision so long as the shape of the reference CT-Q-FMA remains constant throughout use of the measurement system. The manufacture of the mobile Q-FMA may bias measurement system results.

In some examples, a bone rig designed to rigidly connect the reference CT-Q-FMA to the subject bone is manufactured. As shown in FIG. 5, the bone rig is intended to provide a stable relationship between the reference CT-Q-FMA and the subject bone during and between measurements. The bone rig may be composed of CT and MR compatible Objet Digital ABS Polyjet Photopolymer RGD515/535 and may be manufactured on an Objet Connex 500 3D Printer. The manufacture of the bone rig may not affect the measurement system so long as it is able to provide a stable, constant relationship between the Reference CT-Q-FMA and the subject bone throughout use of the measurement system.

In addition, an instrument rig may be used to rigidly connect the mobile Q-FMA and the subject instrument. The instrument rig positions the mobile Q-FMA according to a pre-determined pose with respect to the subject instrument in order to represent the subject instrument in 3D space. The manufacture of the instrument rig may bias measurement system results.

In some examples, subject instrumentation is manufactured and inspected according to certain specifications. Part numbers and quantities involved in each case may vary. In these examples, the manufacture of the subject instrument contributes to the measurement result. Any influence which the manufacturing process may have on intra-operative alignment is captured within the measurement results For pre-imaging assembly, the bone rig is assembled to the subject bone. Aluminum hardware may be used to rigidly attach the Bone Rig to the subject bone in order to be MR and CT compatible and reduce (e.g., minimize) potential of imaging distortion. For instance, two ¼-20 threaded aluminum rods and lock nuts may be positioned and spaced on the subject bone in order to increase (e.g., maximize) stability and reduce (e.g., minimize) the potential of imaging distortion in the proximal and distal epiphyses of the subject bone.

In some implementations, the assembly is designed to maintain a constant relationship with the subject bone and precautions are taken throughout use of the measurement system to preserve that relationship particularly during transport of the patient (e.g., cadaveric specimen used for testing). Bone rig shift relative to the subject bone between or during measurements may bias measurement system results. Zero shift between the bone rig and the subject bone may be assumed throughout use of the measurement system, but shift may be measured post-operatively to confirm and adjust measurements as needed.

To assemble the reference CT-Q-FMA to the bone rig, nylon hardware may be used in order to be CT and MR compatible and reduce (e.g., avoid) image distortion. The assembly may be designed to maintain a constant relationship with the subject bone and precautions may be taken between and during measurement methods to preserve that relationship particularly during transport of the patient (e.g., cadaveric specimen used for testing). Reference CT-Q-FMA shift relative to the subject bone between or during measurements may bias measurement system results. Zero shift between the reference CT-Q-FMA and the subject bone may be assumed throughout use of the measurement system, but shift may be measured post-operatively and accounted for in the final measurement results.

In addition, to CT pre-operative imaging, the portion of the bone (e.g., knee area) is MR imaged with fat-saturation. The fat-saturated MR image is intended to provide a measurement of the articular cartilage thickness, which is absent in the processed CT image. The scan settings are set to be appropriate (per the implant design tool's imaging protocol) for the machine used. The fat-saturation setting is turned on. A deficiency of the fat-saturated MR image may affect measurement system precision.

In some examples, the mean value of the measured cartilage thickness is validated to the literature. MRI machine calibration records defined by the supplier of the MR image may be accessed to account for measurement variation.

The subject bone and reference CT-Q-FMA then may be CT imaged. The following scan settings may be used to generate a sufficient (e.g., optimized) CT image for processing: –25 cm FOV, –0.625 mm helical slice thickness, –0.562 mm helical slice pitch, and –135 mA tube current optimized for bone.

The system 300 treats the CT image of the subject bone and reference CT-Q-FMA as being accurate. CT machine calibration records defined by the supplier of the CT image technology may be accessed to account for imaging variation.

With the assembly shown in FIG. 5, the system may implement a hybrid measurement system which takes advantage of the most accurate pre-operative and intra-operative imaging methods. CT is an accurate imaging tool available to assess anatomic landmarks for use in bone alignment. CT also broadened and enhanced access to bony anatomy when establishing pre-operative alignment targets. Passive reflective markers were still used for intra-operative 3D pose measurement, but optical motion capture measurements were less noisy due to the addition of redundant cameras and markers. The Qualisys ProReflex optical motion cameras used are capable of measuring with micrometer precision. In order to validate that each imaging measurement method was properly calibrated to physical measurements, CMM data may be used to gauge the residual error of the fiducial markers for each method.

In some implementations, independent data from each method is co-registered by matching the reference array of fiducial markers detectable by each of the CT, Qualisys and CMM measurement methods. In these implementations, the reference CT-Q-FMA is rigidly affixed to the subject bone and serves as a reference datum between the pre-operative CT and the intra-operative Qualisys measurements. Because of the role of the reference CT-Q-FMA to the measurement system, it allows independent validation of both CT and Qualisys data to physical CMM measurements. Additionally, intra-operative Qualisys measurements of the resection surface alignment may be validated to match the post-operative CT measured resection surface.

The quality and quantity of data afforded by this hybrid measurement system may improve understanding and ultimately the capability of surgical resection manufacture by design. Accordingly, the techniques described throughout this disclosure may be used to confirm precision of current design processes and may be used to improve design processes in the future.

Referring again to FIG. 4, the system 300 generates a three-dimensional representation of the portion of the bone and the reference fiducial markers based on the pre-operative image data (410). For example, the system 300 generates a three-dimensional solid that includes the portion of the bone and the reference fiducial marker array. In implementations in which the techniques described throughout this disclosure are used in knee implants (e.g., TKA), the system 300 may generate a three-dimensional representation of at least a portion of a femur and/or a tibia. For instance, the system 300 may generate a three-dimensional representation of an entire femur or tibia, or may generate a three-dimensional representation of a portion of the femur or tibia located at the knee joint (e.g., the portion of the femur or tibia that receives an implant during TKA). In addition, the techniques described throughout this disclosure may be applied to other types of implant procedures (e.g., hip replacement, shoulder replacement, etc.). For other types of implant procedures, the system 300 may generate a three-dimensional representation of a portion of the bone that receives the implant, such as a portion of the bone located at a joint associated with the implant procedure.

In some examples, the system 300 may account for cartilage in generating the three-dimensional representation of the portion of the bone. In these examples, the system 300 identifies a measurement for cartilage related to the portion of the bone and adjusts the three-dimensional representation and the coordinate system to account for the identified measurement for cartilage related to the portion of the bone. The system 300 may make an assumption of cartilage thickness based on historical data (e.g., literature on average cartilage thickness for the joint at issue). In addition, the system 300 measure the cartilage thickness by accessing magnetic resonance imaging (MRI) of the portion of the bone and determining a measurement of the cartilage based on the MRI of the portion of the bone.

In processing images to generate the three-dimensional representation, the system 300 may segment the CT image of the subject bone and reference CT-Q-FMA to create a processed CT image using an appropriate software application (e.g., MIMICS software). The system 300 may treat the processed CT image of the subject bone and reference CT-Q-FMA as accurate. The processed CT image of the subject bone and reference CT-Q-FMA may be validated by comparison to CMM measurement of the reference CT-Q-FMA.

The system 300 defines a coordinate system for the three-dimensional representation of the portion of the bone (415) and determines locations of the reference fiducial markers relative to the defined coordinate system (420). The system 300 may define the coordinate system based on user input and/or automated processing. For instance, the system 300 may define the coordinate system based on a user providing user input placing a coordinate axis framework on a portion of the bone. Also, the system 300 may define the coordinate system automatically by identifying one or more landmarks on the portion of the bone and defining the coordinate system relative to the one or more identified landmarks.

The system 300 may define the coordinate system at any position and orientation of the bone as long as the coordinate system enables measurements of locations of the fiducial markers and co-registration of the multiple modalities of imaging technology, discussed in more detail below. For example, in TKA, the femur mechanical axis may be established using proximal and distal mechanical points defined by the centers of the proximal and distal joints and the femur mechanical axis may be defined as the Z-axis of the femur coordinate system. In this example, the tibia mechanical axis may be established using proximal and distal mechanical points defining the centers of the proximal and distal joints and the tibia mechanical axis may be defined as the Z-axis of the tibia coordinate system.

After defining the coordinate system, the system 300 determines locations of the fiducial markers in terms of the defined coordinate system. For example, the reference fiducial markers may be radio-opaque, infrared reflective spherical markers and the reference fiducial marker array may include at least five reference spherical markers. In this example, the system 300 determines a location for each of the at least five reference spherical markers. In determining locations, the system 300 may determine centers of the reference spherical markers and may determine locations of the reference fiducial markers as the determined centers of the reference spherical markers. In addition, the system 300 may identify the reference spherical markers, regression fit each of the identified reference spherical markers with an ideal sphere shape, and determine locations of the reference spherical markers using the regression-fitted reference spherical markers.

In some implementations, the system 300 validates the determined locations of the reference fiducial markers. In these implementations, the system 300 may access CMM data for the reference fiducial marker array and validate the determined locations of the reference fiducial markers using the accessed CMM data for the reference fiducial marker array. The validation may involve a comparison of the relative locations of the reference fiducial markers in the CMM data against the relative locations of the reference fiducial markers as determined using the image data. The system 300 may continue processing if the comparison reveals that the determined locations are within a threshold of the expected locations. If the comparison reveals that the determined locations are outside of a threshold of the expected locations, the imaging system may be recalibrated and the imaging may be repeated.

Figure 6:
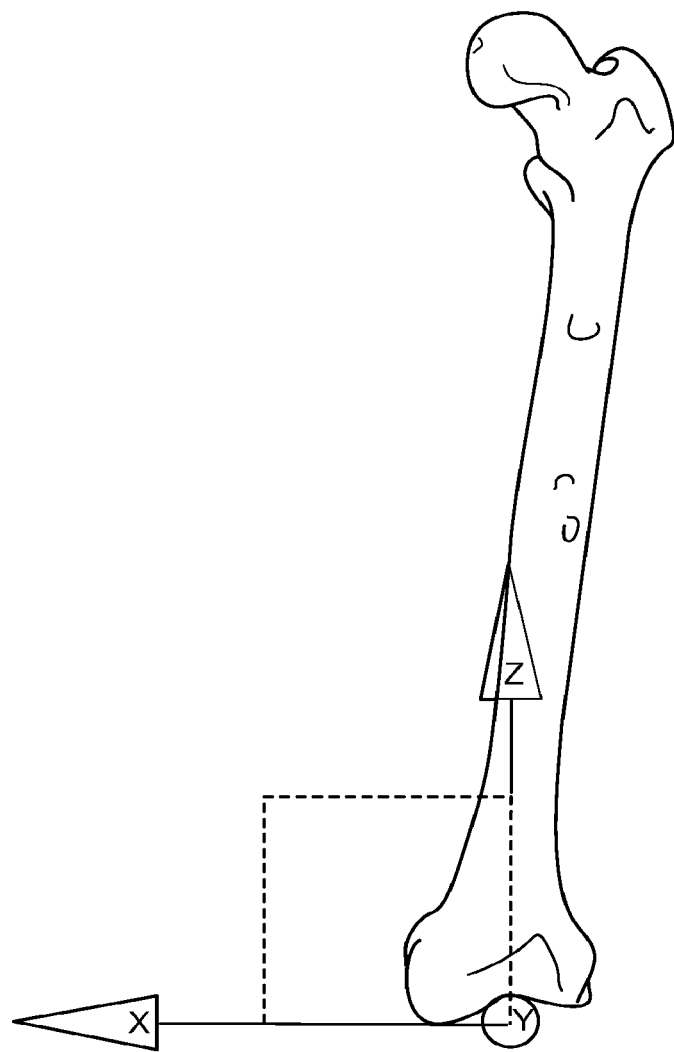
FIGS. 6-9 are diagrams illustrating example alignment axes for bone segments.
Figure 7:
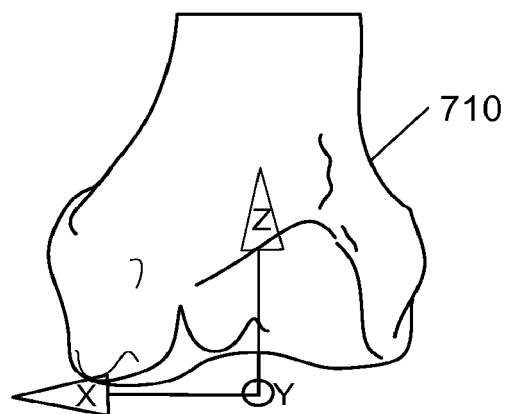
Figure 7:
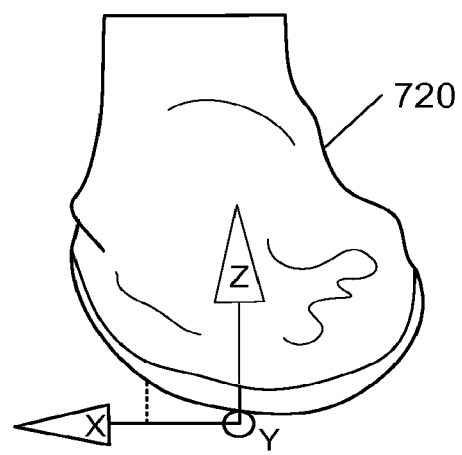
Figure 7:
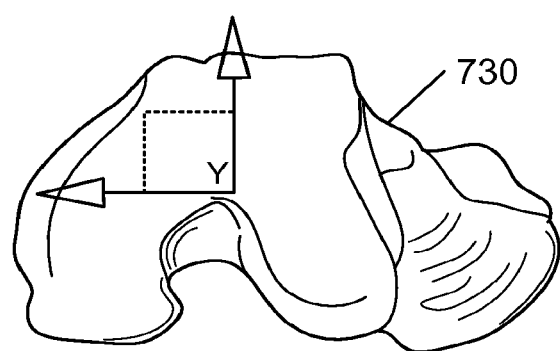

FIGS. 6-9 illustrate example alignment axes for bone segments. FIGS. 6 and 7 illustrate multiple views of anatomic alignment axes defined by the system 300 for a femur. The gap between the coordinate system's origin and the bone represents the cartilage thickness on the preferred distal condyle. As shown in FIG. 6, the three-dimensional representation 600 includes an entire femur with a coordinate system defined with the Z-axis aligning with a mechanical axis of the femur. FIG. 7 illustrates multiple views of the three-dimensional representation 600 focused on the portion of the femur relevant to a TKA procedure. As shown, a first view 710 illustrates the Z and X axes defined relative to the bone, a second view 720 illustrates the Z and Y axes defined relative to the bone, and a third view 730 illustrates the X and Y axes defined relative to the bone.

Figure 8:
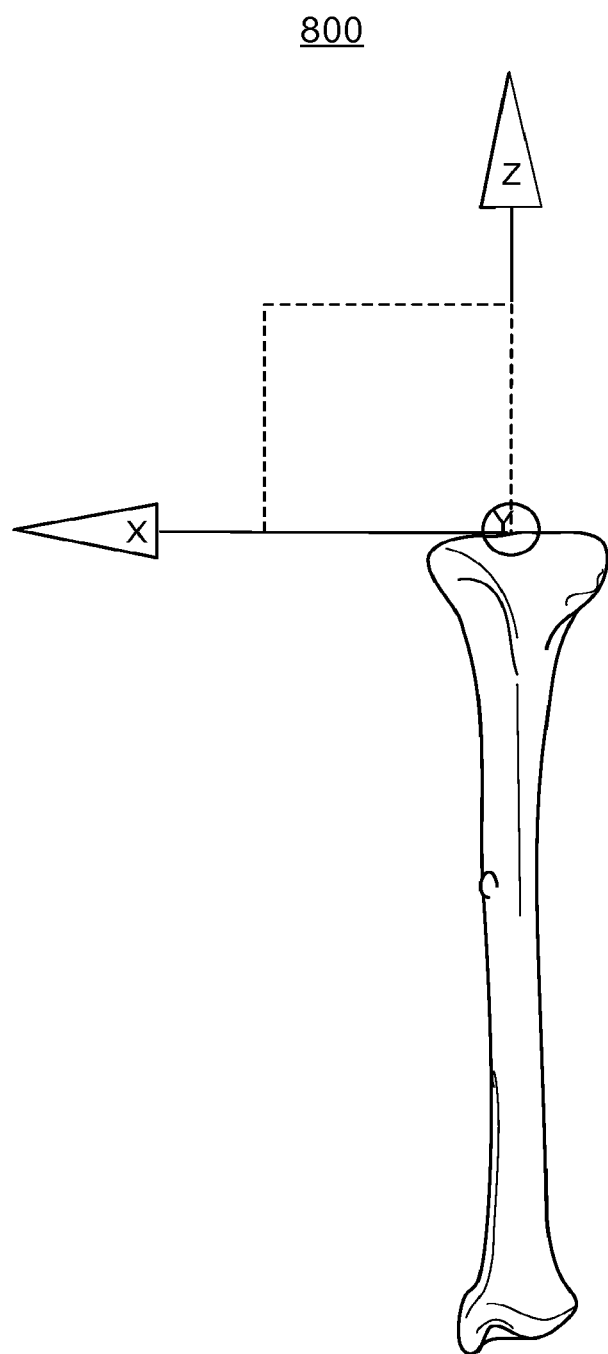
Figure 9:
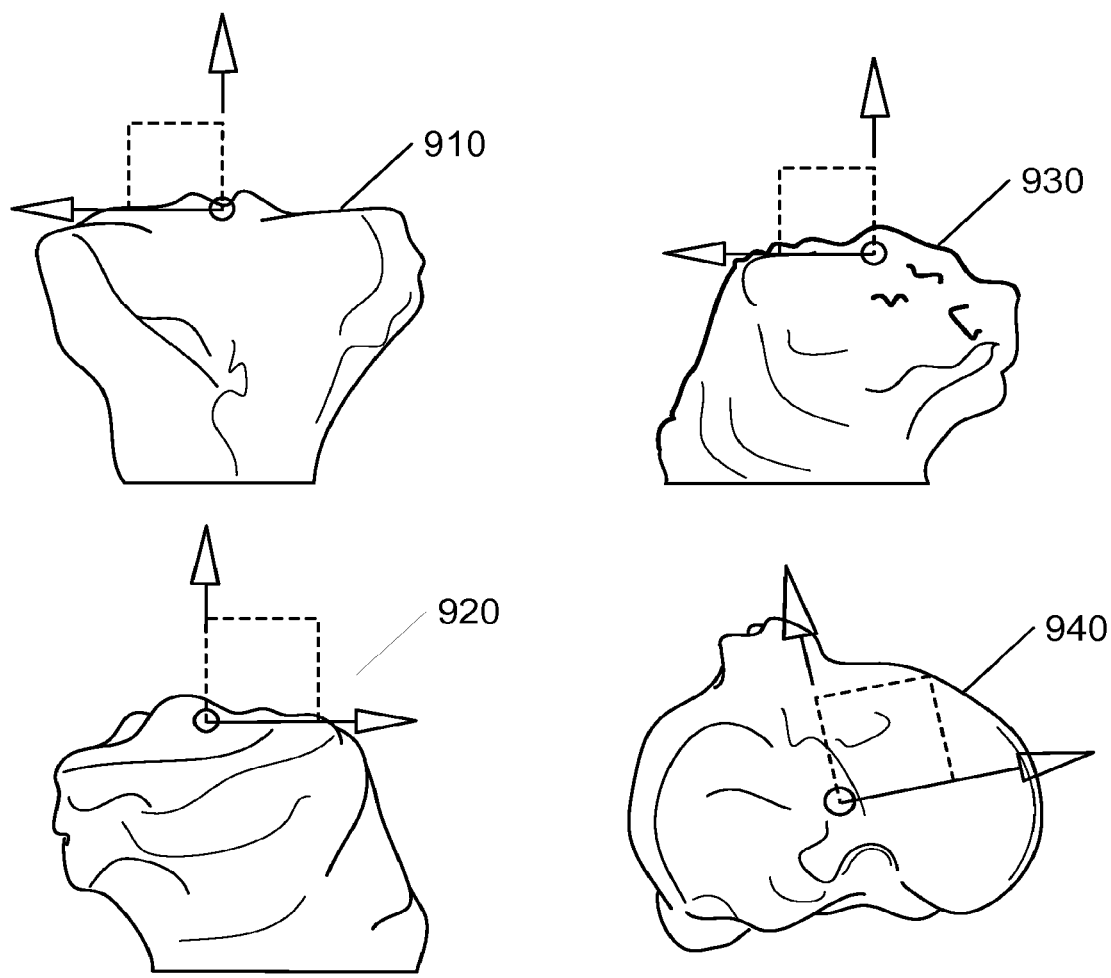

FIGS. 8 and 9 illustrate multiple views of anatomic alignment axes defined by the system 300 for a tibia. The gap between the coordinate system's origin and the bone represents the cartilage thickness at the resection reference point. As shown in FIG. 8, the three-dimensional representation 800 includes an entire tibia with a coordinate system defined with the Z-axis aligning with a mechanical axis of the tibia. FIG. 9 illustrates multiple views of the three-dimensional representation 800 focused on the portion of the tibia relevant to a TKA procedure. As shown, a first view 910 illustrates the Z and X axes defined relative to the bone, second and third views 920 and 930 illustrate the Z and Y axes defined relative to the bone, and a fourth view 940 illustrates the X and Y axes defined relative to the bone.

Referring again to FIG. 4, the system 300 accesses intra-operative image data that includes the portion of the bone to which to the reference fiducial marker array is fixed and a mobile fiducial marker array that is attached to an instrument used in a surgical procedure on the portion of the bone (425). The mobile fiducial marker array may include at least three mobile fiducial markers and the intra-operative image data may be captured using a second imaging modality that is different than the first imaging modality and that is configured to image the reference fiducial markers and the mobile fiducial markers. For instance, the system 300 may access intra-operative motion capture data that includes the portion of the bone to which to the reference fiducial marker array is fixed and the mobile fiducial marker array that is attached to the instrument used in the surgical procedure on the portion of the bone.

In implementations in which the techniques described throughout this disclosure are used in knee implants (e.g., TKA), the system 300 accesses intra-operative image data of at least a portion of a femur and/or a tibia. For instance, the system 300 may access intra-operative image data of an entire femur or tibia, or may access pre-operative image data of a portion of the femur or tibia located at the knee joint (e.g., the portion of the femur or tibia that receives an implant during TKA). In addition, the techniques described throughout this disclosure may be applied to other types of implant procedures (e.g., hip replacement, shoulder replacement, etc.). For other types of implant procedures, the system 300 may access intra-operative image data of a portion of the bone that receives the implant, such as a portion of the bone located at a joint associated with the implant procedure.

In TKA implementations, the instrument used in the surgical procedure may be a cutting block. In these implementations, the mobile fiducial marker array may be attached to the cutting block through the cutting slot of the cutting block and at least one other portion of the cutting block. For instance, the mobile fiducial marker array may be attached to the cutting block through the cutting slot of the cutting block and at least one pin hole of the cutting block. In addition, the mobile fiducial marker array may be attached to the cutting block through the cutting slot using a surgical blade designed to be inserted through the cutting slot and one or more shims that rigidly support the surgical blade in the cutting slot.

In terms of non-destructive testing, the mobile Q-FMA may be used to represent the 3D pose of the subject instrument during intra-operative motion capture (e.g., ProReflex motion capture technology provided by Qualisys AB) measurements. The mobile Q-FMA may be mated to the instrument rig and the instrument rig may be mated to alignment features of the subject instrument. The instrument rig may be intended to maintain a pre-determined 3D pose between the mobile Q-FMA and the subject instrument. Assembly variation around the pre-determined 3D pose between the mobile Q-FMA and the subject instrument may affect measurement system precision and may be accounted for in the results output.

After mating the instrument rig to alignment features of the subject instrument, the subject instrument may be physically aligned to the subject bone. Motion capture (e.g., ProReflex motion capture technology provided by Qualisys AB) may measure the 3D pose of the mobile Q-FMA with respect to the reference CT-Q-FMA. For example, an incision may be made and the subject bone may be exposed. With the reference CT-Q-FMA and the mobile Q-FMA visible to the motion capture cameras, the surgical operator aligns the subject instrument to the subject bone. Once the surgical operator is confident in the alignment of the subject instrument, the motion capture cameras capture the 3D pose of the mobile Q-FMA with respect to the reference CT-Q-FMA. These steps may be repeated as needed for additional instruments. Precision of the intra-operative alignment of the subject instrument to the subject bone is a component of the measurement system result.

Figure 12:
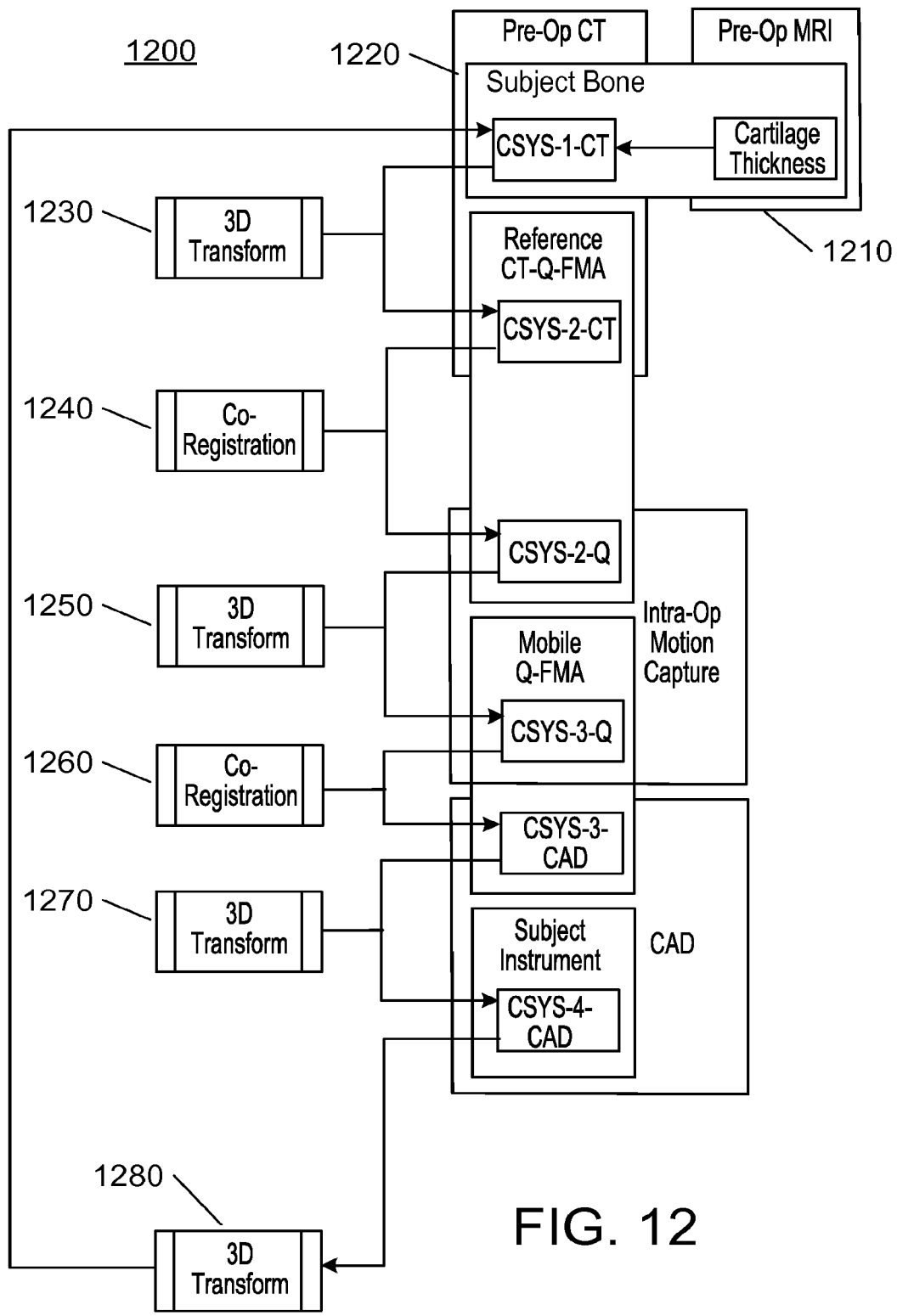

The system 300 co-registers the intra-operative image data with the three-dimensional representation of the portion of the bone by matching the reference fiducial markers included in the intra-operative image data to the determined locations of the reference fiducial markers relative to the defined coordinate system (430). For example, the system 300 determines locations of the reference fiducial markers included in the intra-operative image data using techniques discussed above with respect to reference numeral 420. In this example, the system 300 takes the determined locations of the reference fiducial markers in the intra-operative image data, matches the determined locations of the reference fiducial markers in the intra-operative image data to the determined locations of the reference fiducial markers in the pre-operative image data, and overlays the intra-operative image data onto the pre-operative image data based on the matching. To the extent that the determined locations of the reference fiducial markers in the intra-operative image data do not exactly match the determined locations of the reference fiducial markers in the pre-operative image data, the system 300 evaluates the best fit and matches the locations in a manner that minimizes the aggregate differences between the locations. FIG. 12, discussed below, describes additional details of co-registration in TKA implementations.

Figure 10:
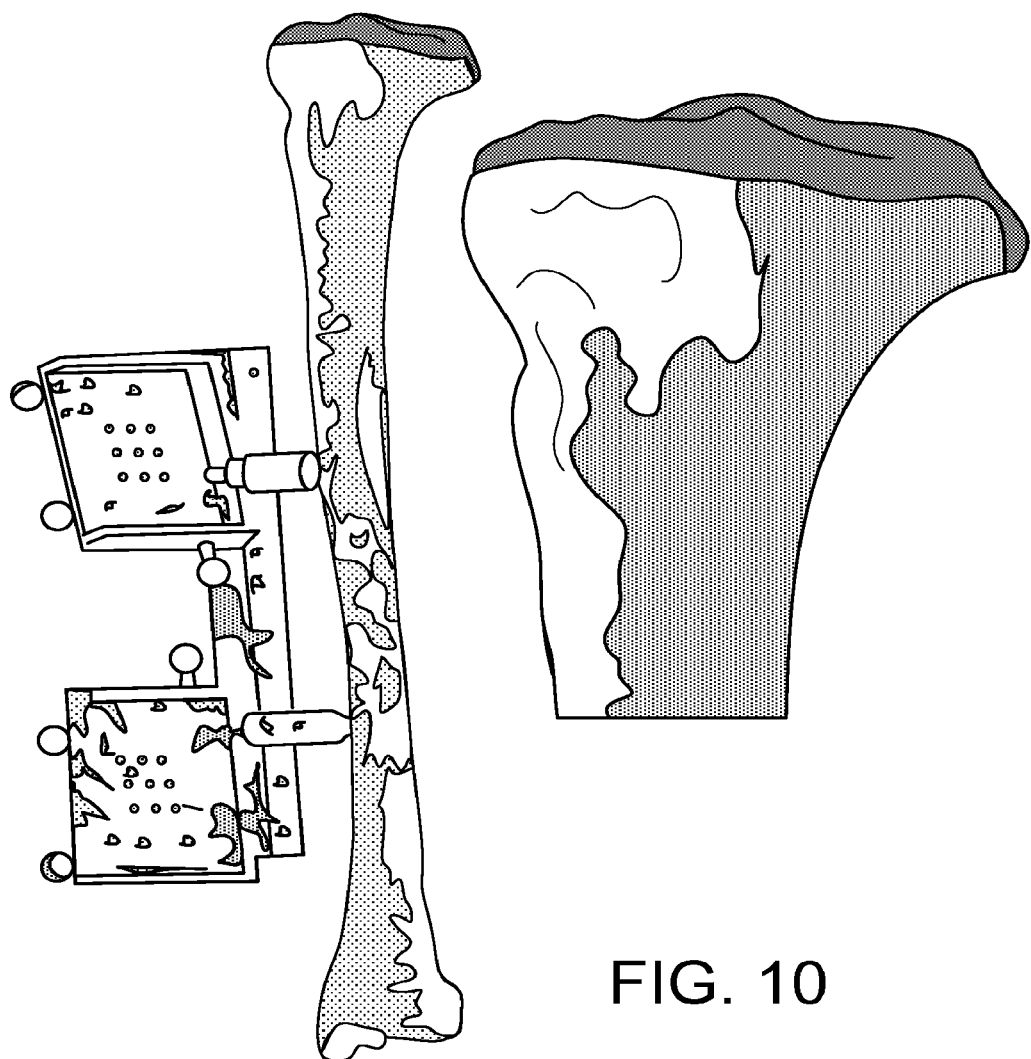
FIGS. 10 and 11 are diagrams illustrating example co-registered and overlaid pre- and post-operative images.
Figure 11:
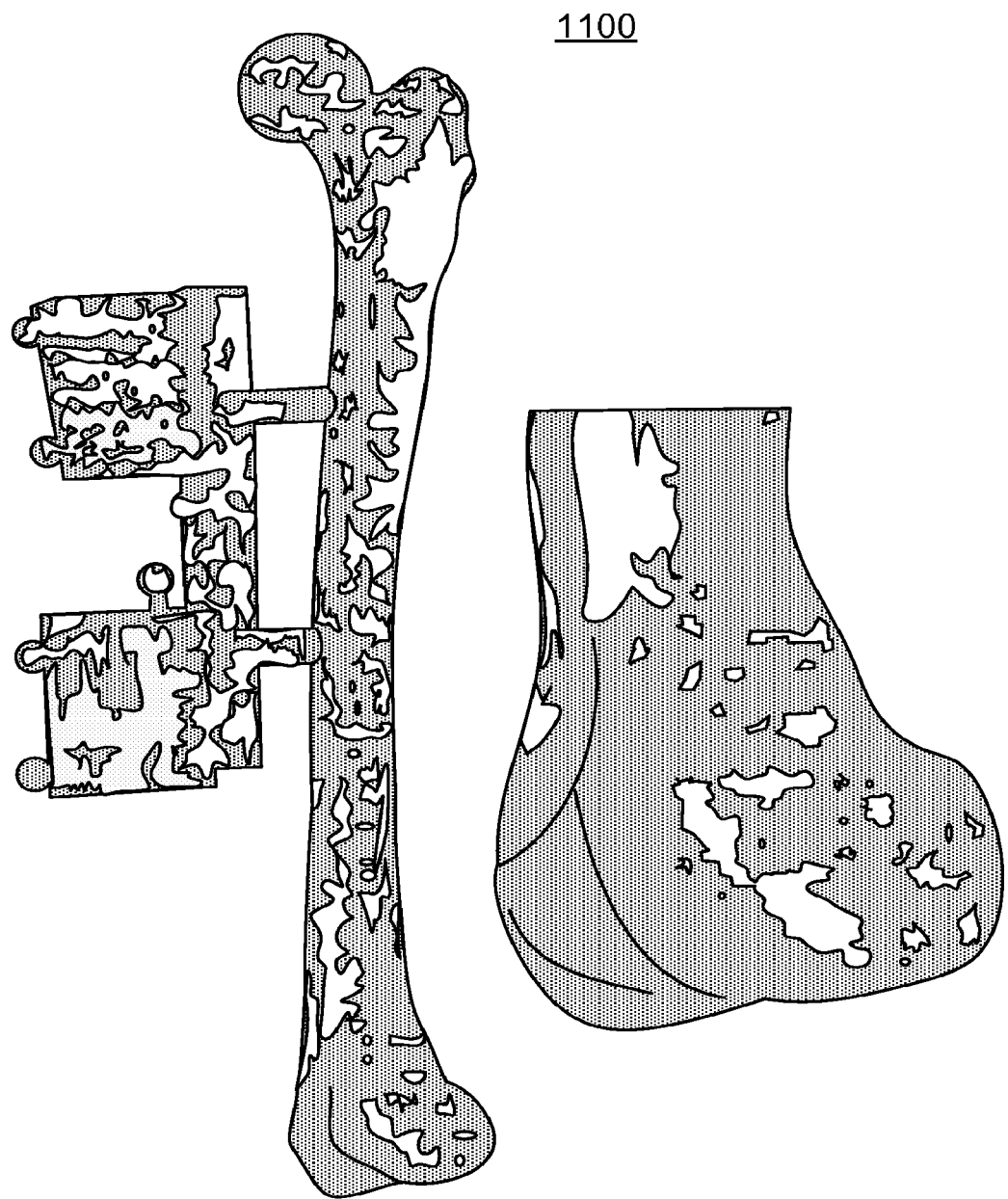

FIGS. 10 and 11 illustrate example co-registered and overlaid pre- and post-operative images. FIG. 10 illustrates an example image 1000 of a tibia and FIG. 11 illustrates an example image 1100 of a femur. In each of the images 1000 and 1100, the differences are illustrated by shading.

Referring again to FIG. 4, the system 300 determines locations of the mobile fiducial markers in the co-registered intra-operative image data and three-dimensional representation of the portion of the bone (435). The system 300 may determine locations of the fiducial markers in terms of the defined coordinate system. For example, the mobile fiducial markers may be radio-opaque, infrared reflective spherical markers and the mobile fiducial marker array may include at least five reference spherical markers. In this example, the system 300 determines a location for each of the at least five mobile spherical markers. In determining locations, the system 300 may determine centers of the mobile spherical markers and may determine locations of the mobile fiducial markers as the determined centers of the mobile spherical markers. In addition, the system 300 may identify the mobile spherical markers, regression fit each of the identified mobile spherical markers with an ideal sphere shape, and determine locations of the mobile spherical markers using the regression-fitted mobile spherical markers.

In some implementations, the system 300 validates the determined locations of the mobile fiducial markers. In these implementations, the system 300 may access CMM data for the mobile fiducial marker array and validate the determined locations of the mobile fiducial markers using the accessed CMM data for the mobile fiducial marker array. The validation may involve a comparison of the relative locations of the mobile fiducial markers in the CMM data against the relative locations of the mobile fiducial markers as determined using the image data. The system 300 may continue processing if the comparison reveals that the determined locations are within a threshold of the expected locations. If the comparison reveals that the determined locations are outside of a threshold of the expected locations, the imaging system may be recalibrated and the imaging may be repeated.

The system 300 determines a three-dimensional spatial position and orientation of the instrument relative to the portion of the bone based on the determined locations of the mobile fiducial markers (440). For example, the system 300 may use a computer-aided-design (CAD) model to determine the known relationship between the instrument and the mobile fiducial markers. In this example, the system 300 accesses data defining three-dimensional spatial position and orientation of the instrument relative to the mobile fiducial markers determined using the CAD model of the instrument with the mobile fiducial marker array attached and determines the three-dimensional spatial position and orientation of the instrument relative to the portion of the bone by mapping the three-dimensional spatial position and orientation of the instrument relative to the mobile fiducial markers to the determined locations of the mobile fiducial markers. In this regard, the system 300 uses the known relationship of the instrument to the mobile fiducial markers to determine the position and orientation of the instrument relative to the portion of the bone.

In another example, the system 300 may use CMM data to determine the known relationship between the instrument and the mobile fiducial markers. In this example, the system 300 accesses data defining three-dimensional spatial position and orientation of the instrument relative to the mobile fiducial markers determined CMM evaluation of the instrument with the mobile fiducial marker array attached and determines the three-dimensional spatial position and orientation of the instrument relative to the portion of the bone by mapping the three-dimensional spatial position and orientation of the instrument relative to the mobile fiducial markers to the determined locations of the mobile fiducial markers. In this regard, the system 300 uses the known relationship of the instrument to the mobile fiducial markers to determine the position and orientation of the instrument relative to the portion of the bone.

The system 300 compares the three-dimensional spatial position and orientation of the instrument relative to the portion of the bone with a designed alignment of the instrument to the portion of the bone (445). For example, the system 300 accesses, from electronic storage, a designed alignment of the instrument to the portion of the bone from the pre-surgical alignment design for the surgical procedure. In this example, the system 300 compares a three-dimensional spatial position and orientation of the instrument in the designed alignment with the three-dimensional spatial position and orientation of the instrument in the co-registered images. Based on the comparison, the system 300 determines differences between the position of the instrument in the design relative to the intra-operative position of the instrument captured in the co-registered images.

In performing the comparison, the system 300 may match the pre-surgical alignment design for the instrument to the co-registered images and, based on the matching, overlay the pre-surgical alignment design for the instrument onto the co-registered images. After the pre-surgical alignment design for the instrument is overlaid on the co-registered images, the system 300 may directly compare the designed alignment to the measured intra-operative alignment and identify areas where the designed alignment and the measured intra-operative alignment overlap and areas where the designed alignment and the measured intra-operative alignment do not overlap.

Based on comparison results, the system 300 determines an indication of precision of alignment of the instrument in the surgical procedure on the portion of the bone relative to the designed alignment of the instrument to the portion of the bone (450). For example, based on the comparison, the system 300 identifies differences in the measured intra-operative alignment and the designed alignment. In this example, the system 300 analyzes the identified differences and determines an indication of precision of alignment of the instrument in the surgical procedure based on the analysis. For instance, the system 300 may determine a percentage that the measured intra-operative alignment overlaps with the designed alignment. In addition, the system 300 may identify spaces between an edge of the instrument in the measured intra-operative alignment and an edge of the instrument in the designed alignment. The system 300 may, as part of the indication, determine a mean and/or median distance among the spaces or determine a maximum and/or minimum distance among the spaces. The system 300 may use any type of indication of precision of alignment. In implementations in which the techniques described throughout this disclosure are used in knee implants (e.g., TKA), the system 300 may assess the precision relative to the planes of resection cuts in the measured intra-operative alignment as compared to the planes of resection cuts in the designed alignment.

The system 300 provides output based on the determined indication of precision of alignment of the instrument in the surgical procedure relative to the designed alignment of the instrument (455). For example, the system 300 may provide output that indicates the alignment precision in the surgical procedure. In this example, the system 300 may output a percentage of the alignment fit and/or output a tolerance measurement that indicates how closely the alignment matches (e.g., matches within two millimeters). The system 300 may store the output to indicate how well the surgical procedure was performed by the surgeon.

In providing output, the system 300 may be used in surgical procedures involving cadaver patients, rather than during surgery on a live patient. In these cases, the setup and use of a bone rig is used to improve the design process and determine precision in the alignment process. Accordingly, the output provided by the system 300 is used to validate the patient-matched design process on the cadaver patient and the post-operative imaging is used to improve future results on live patients via surgeon feedback. In this regard, the system 300 may provide the output by simply storing the results of the measurements and analysis, rather than displaying the output live during the surgical procedure. The system 300 then may later access the stored output, perform analysis on the accessed output, and display the accessed output and/or results of the analysis on the accessed output.

In some implementations, the system 300 may compute statistics related to general alignment precision for the process used in the surgical procedure. In these implementations, the system 300 aggregates the determined indication of precision of alignment of the instrument in the surgical procedure relative to the designed alignment of the instrument with similar data determined from other similar surgical procedures. The system 300 then performs statistical analysis of the aggregated data, determines a representation of general alignment precision in surgical procedures included in the aggregated data based on the statistical analysis of the aggregated data, and provides output indicating the determined representation of general alignment precision. For instance, the system 300 may compute a mean precision, a median precision, or any other statistical indication of the general alignment precision for the process used in the surgical procedure. In this regard, the system 300 may perform a T test and/or F test statistical analysis on the aggregated data and output the results of the T test and/or F test statistical analysis.

Figure 13:
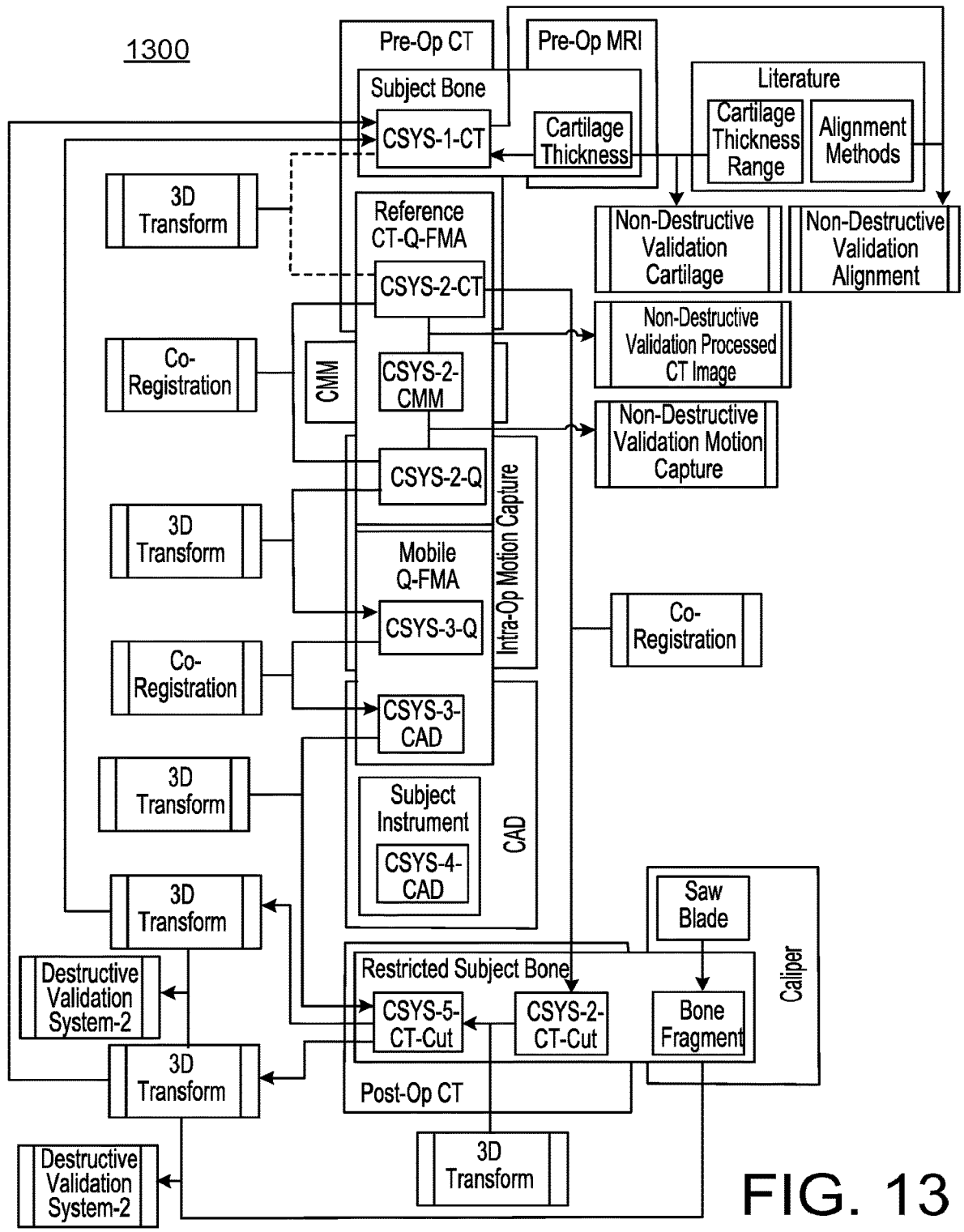

In some examples, the system 300 uses post-operative data to validate the alignment precision determined through use of the intra-operative image data. In these examples, the system 300 may access data descriptive of post-operative validation of cuts made during the surgical procedure and validate the determined indication of precision of alignment based on the accessed data descriptive of post-operative validation of cuts made during the surgical procedure. The post-operative data may include either non-destructive imaging data for any patients and/or destructive validation data (e.g., caliper measurements) for cadaveric subjects. FIG. 13, discussed below, describes post-operative measurement validation in more detail as it relates to validating precision in TKA procedures.

FIG. 12 illustrates an example of a process 1200 for analyzing non-destructive measurement system results. The operations of the process 1200 are described generally as being performed by the system 300. In some implementations, operations of the process 1200 may be performed by one or more processors included in one or more electronic devices. The process 1200 illustrates an example of processing that may be performed as part of or in conjunction with the process 400 using the assembly shown in FIG. 5.

As discussed above with respect to FIG. 4, the system 300 accesses an MRI image of the subject bone and uses the MRI image to determine cartilage thickness (1210). In addition, the system 300 accesses a CT image of the subject bone (i.e., CSYS-1-CT) and determines a coordinate system for the CT image (1220).

The system 300 then calculates a 3D transformation between CSYS-1-CT and CSYS-2-CT (1230). As mentioned above, CSYS-1-CT is defined as the CT image with a coordinate system defined. CSYS-2-CT is defined by the sphere pattern of the reference CT-Q-FMA as measured by the processed CT image.

In some examples, each surface representing a reference CT-Q-FMA sphere in the processed CT image is identified and regression-fitted with an ideal sphere. In these examples, the pattern of regression-fitted ideal spheres defines CSYS-2-CT. The processed CT image of the reference CT-Q-FMA may be assumed to be accurate. Also, the processed CT image of the reference CT-Q-FMA may be validated by comparison to CMM measurement of the reference CT-Q-FMA.

The system 300 co-registers CSYS-2-CT with CSYS-2-Q (1240). CSYS-2-Q is defined by the sphere pattern of the reference CT-Q-FMA as measured by motion capture (e.g., ProReflex motion capture technology provided by Qualisys AB). Each [x,y,z] point measured by motion capture represents the center of one sphere of the reference CT-Q-FMA. The pattern of [x,y,z] points defines CSYS-2-Q in the same way that the pattern of regression fitted ideal spheres defines CSYS-2-CT. The sphere pattern defining CSYS-2-Q is regression-fitted to the sphere pattern defining CSYS-2-CT.

Residual pattern fit error may affect measurement system precision, but is inherently captured in the precision measurement that follows.

The system 300 calculates each 3D transformation between CSYS-2-Q and CSYS-3-Q (1250). CSYS-2-Q is already defined as discussed above. CSYS-3-Q is defined by the sphere pattern of the mobile Q-FMA as measured by motion capture (e.g., ProReflex motion capture technology provided by Qualisys AB). Each [x,y,z] point measured by motion capture represents the center of one sphere of the mobile Q-FMA. The pattern of [x,y,z] points defines CSYS-3-Q. Each intra-operative subject instrument alignment measurement made with motion capture is calculated as one transformation between CSYS-2-Q and CSYS-3-Q.

In some implementations, this 3D transformation is subject to motion capture measurement noise because there is a limit, however small, to the precision with which motion capture can determine the [x,y,z] of a particular sphere. Measurement precision has several physical influences, and the system 300 attempts to minimize measurement noise by addressing those physical causes. For instance, the system 300 uses redundant motion capture cameras, redundant fiducial markers, appropriately sized and spaced fiducial markers per the measurement volume, and calibration prior to motion capture usage.

To measure motion capture precision, the motion captures are made of the reference CT-Q-FMA and the mobile Q-FMA where the mobile Q-FMA is known to be stationary with respect to the reference CT-Q-FMA (e.g., fixed in place with no human influence). Recorded alignment fluctuations of the mobile Q-FMA with respect to the reference CT-Q-FMA may be measured as motion capture measurement precision, which can affect measurement system precision. The system 300 may account for the motion capture precision in the results outputted.

The system 300 co-registers CSYS-3-Q with CSYS-3-CAD (1260). CSYS-3-Q is defined as discussed above. CSYS-3-CAD is defined by the sphere pattern of a computer aided design (CAD) model of the mobile Q-FMA. The sphere pattern defining CSYS-3-Q is regression-fitted to the sphere pattern defining CSYS-3-CAD.

In these examples, residual pattern fit error may affect measurement system precision, but is inherently captured in the precision measurement of the prior operations. Manufacturing deviations of the mobile Q-FMA may contribute to residual pattern fit error, which may bias measurement system results.

The system 300 calculates the 3D transformation between CSYS-3-CAD and CSYS-4-CAD (1270). CSYS-3-CAD is defined as discussed above. CSYS-4-CAD is defined by the subject instrument alignment typically associated with subject instrument features, such as a cutting slot, pin holes, reference lines, etc. The 3D transformation between CSYS-3-CAD and CSYS-4-CAD is known as it is predetermined by the design of the instrument rig which positions and orients the mobile Q-FMA to the subject instrument. In this regard, the position of the instrument is aligned to the subject bone based on the images of the fiducial markers of the mobile Q-FMA and the known relationship of the instrument to the fiducial markers of the mobile Q-FMA, as defined by CSYS-4-CAD.

In some examples, manufacturing accuracy of the instrument fixture may bias measurement system results. Assembly variation of the mobile Q-FMA, instrument fixture and subject instrument may affect measurement system precision. In addition, manufacturing accuracy of the subject instrument(s) is a component of the measurement system results. Accordingly, the accuracy and precision of each phase of the surgical procedure and non-destructive analysis may be taken into account and used in the output provided by the system 300.

The system 300 calculates the 3D transformation(s) between CSYS-4-CAD and CSYS-1-CT (1280). The 3D transformation(s) between CSYS-4-CAD and CSYS-1-CT (1280) may be calculated using previously calculated 3D transformations or co-registrations. These 3D transformations are the results of the measurement system.

FIG. 13 illustrates an example of a process 1300 for analyzing destructive measurement system validation results. The operations of the process 1300 are described generally as being performed by the system 300. In some implementations, operations of the process 1300 may be performed by one or more processors included in one or more electronic devices. The process 1300 illustrates an example of processing that may be performed as part of or in conjunction with the process 400 using the assembly shown in FIG. 5.

After completion of all non-destructive testing using the measurement system, the subject bone is resected for destructive validation of the measurement system. Calipers may be used to measure the thickness of the resected subject bone fragment from the resected surface to the articular cartilage reference used to determine the resection depth. The subject bone fragment measurement does not include the saw-blade thickness. Accordingly, the system 300 combines the subject bone fragment caliper measurement with the saw-blade caliper measurement and records them together.

The system 300 calculates the 3D transformation between CSYS-1-CT and CSYS-5-CT-Cut. CSYS-1-CT as discussed above with respect to FIG. 12.

CSYS-5-CT-Cut is defined on the resected surface of the subject bone in the post-operative processed CT image. A post-operative CT image of the resected subject bone and reference CT-Q-FMA is obtained and processed using the same methods as the pre-operative CT imaging and processing. The pre- and post-operative processed CT images are co-registered with each other by regression-fitting the sphere pattern of the Reference CT-Q-FMA present in each processed image. The 3D transformation between CSYS-1-CT and CSYS-5-CT-Cut is the independent post-operative CT measure of the resection surface alignment, which will be compared with the results of the measurement system.

In some implementations, each [x,y,z] point measured by motion capture (e.g., ProReflex motion capture technology provided by Qualisys AB) represents the center of one sphere of the reference CT-Q-FMA. The sphere pattern is regression-fitted to the CMM sphere pattern. Residual pattern fit error is recorded by the system 300. Articular cartilage thickness of the subject bone as measured in the fat-saturated MR image is compared to the literature reported range of articular cartilage in the corresponding region. Articular cartilage measurements and the literature reported range are recorded by the system 300.

With the data recorded in the process 1300, the system 300 validates each phase of the measurement process. The system 300 then may validate the entire measurement process and determine the degree of precision in the measurements, which the system 300 may output as part of the results.

Figure 14:
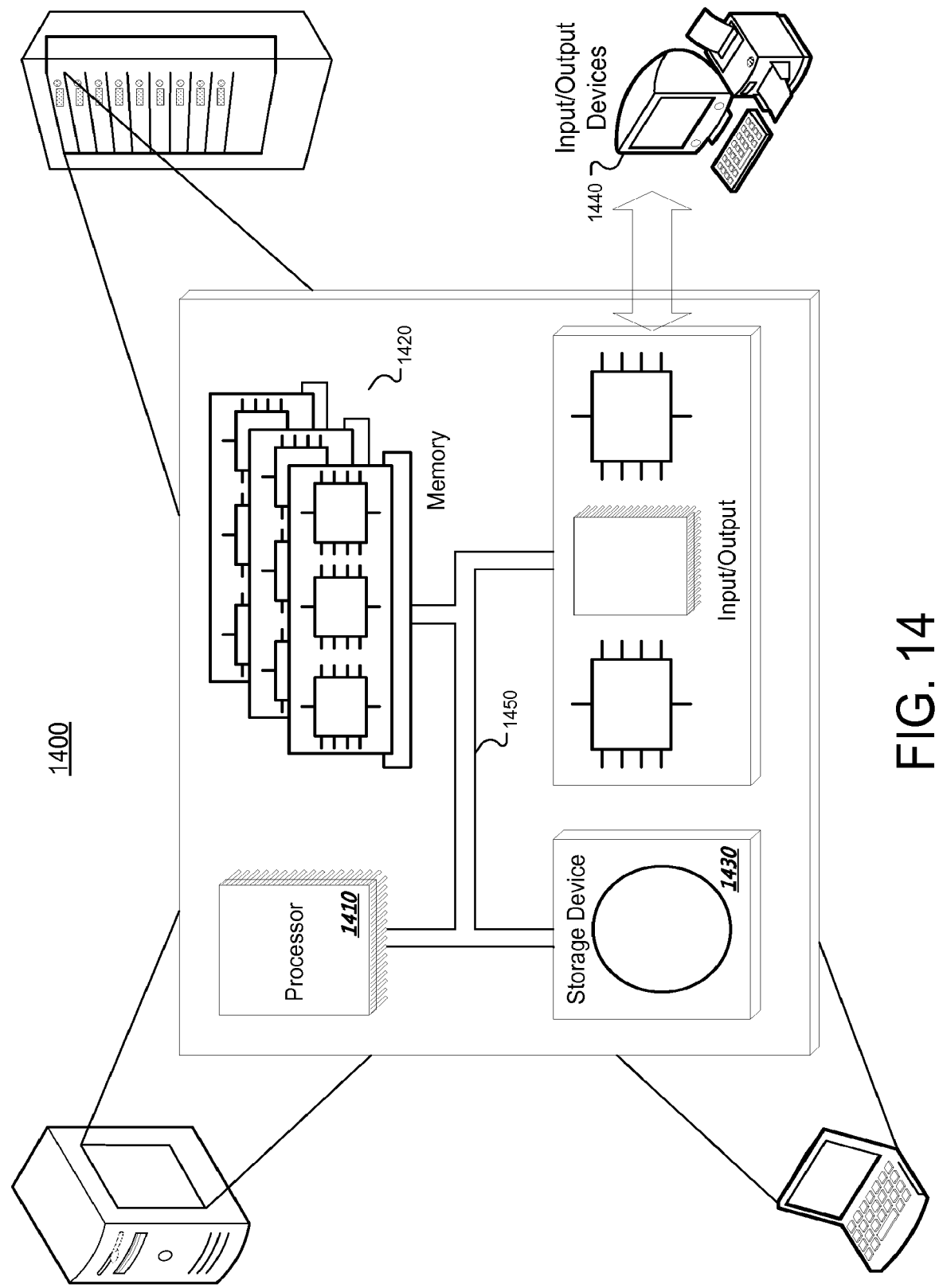

FIG. 14 illustrates an example of a generic computer system 1400. The system 1400 can be used for the operations described in association with the processes 100, 200, 400, 1200, and 1300, according to some implementations. The system 1400 may be included in the system 400.

The system 1400 includes a processor 1410, a memory 1420, a storage device 1430, and an input/output device 1440. Each of the components 1410, 1420, 1430, and 1440 are interconnected using a system bus 1450. The processor 1410 is capable of processing instructions for execution within the system 1400. In one implementation, the processor 1410 is a single-threaded processor. In another implementation, the processor 1410 is a multi-threaded processor. The processor 1410 is capable of processing instructions stored in the memory 1420 or on the storage device 1430 to display graphical information for a user interface on the input/output device 1440.

The memory 1420 stores information within the system 1400. In one implementation, the memory 1420 is a computer-readable medium. In one implementation, the memory 1420 is a volatile memory unit. In another implementation, the memory 1420 is a non-volatile memory unit.

The storage device 1430 is capable of providing mass storage for the system 1400. In one implementation, the storage device 1430 is a computer-readable medium. In various different implementations, the storage device 1430 may be a floppy disk device, a hard disk device, an optical disk device, or a tape device.

The input/output device 1440 provides input/output operations for the system 1400. In one implementation, the input/output device 1440 includes a keyboard and/or pointing device. In another implementation, the input/output device 1440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The tangible computer-readable mediums described throughout this disclosure may be referred to as non-transitory computer-readable mediums. Non-transitory computer-readable mediums may include any type of hardware storage device and the term non-transitory may be used to distinguish from intangible information carriers, such as propagating signals.

A number of implementations have been described. Nevertheless, it will be understood that various modifications may be made without departing from the spirit and scope of the disclosure. Accordingly, other implementations are within the scope of the following claims.

What is claimed is:

1. A non-destructive method of validating a surgical alignment, the method comprising:
   obtaining a pre-operative plan comprising pre-operative image data that includes a first portion of a patient bone and one or more fiducial markers, wherein the one or more fiducial markers comprise at least one of one or more reference fiducial markers and one or more mobile fiducial markers;
   obtaining post-operative image data that includes at least a second portion of the patient bone and the one or more fiducial markers;
   co-registering the post-operative image data to the pre-operative image data based on at least one of:
   a spatial position and orientation of one or more anatomical landmarks on the first and second portion of the patient bone;
   a spatial position and orientation of the one or more reference fiducial markers relative to the first and second portion of the patient bone;
   an intra-operative motion capture image data of the patient bone and the one or more fiducial markers;

a spatial position and orientation of the one or more fiducial markers in pre-operative image data relative to the one or more fiducial markers in the post-operative image data, based on an operative device design; and a spatial position and orientation of the one or more mobile fiducial markers relative to a surgical instrument;

generating, based on the co-registration, an alignment image comprising an intra-operative alignment of the surgical instrument with the patient bone;

determining, based on the alignment image, an accuracy measurement of the intra-operative alignment with respect to the pre-operative plan.

2. The method of claim 1, wherein the pre-operative image data includes an MRI image comprising a cartilage thickness of the patient.

3. The method of claim 2, further comprising defining one or more coordinate systems for the post-operative image data accounting for the cartilage thickness of the patient.

4. The method of claim 3, wherein the one or more coordinate systems comprises a coordinate system for a femur of the patient and a coordinate system for a tibia of the patient.

5. The method of claim 3, wherein co-registering the post-operative image data to the pre-operative image data comprises regression fitting the spatial position and orientation of the one or more fiducial markers in the pre-operative image data relative to the one or more fiducial markers in the post-operative image data.

6. The method of claim 5, further comprising processing the post-operative image data by calculating a three-dimensional transformation based on the one or more coordinate systems and the one or more reference fiducial markers.

7. The method of claim 1, further comprising processing the intra-operative motion capture image data by calculating a three-dimensional transformation based on the post-operative image data and the one or more mobile fiducial markers.

8. The method of claim 1, wherein determining an accuracy measurement comprises comparing the intra-operative alignment to a designed alignment of the pre-operative plan.

9. The method of claim 8, wherein the accuracy measurement comprises a percentage fit between the intra-operative alignment and the designed alignment.

10. The method of claim 8, wherein the accuracy measurement comprises a tolerance measurement between the intra-operative alignment and the designed alignment.

11. The method of claim 1, wherein the one or more reference fiducial markers comprise at least three reference fiducial markers.

12. The method of claim 1, wherein the one or more mobile fiducial markers comprise at least three mobile fiducial markers.

13. A destructive method of validating a surgical alignment, the method comprising:

obtaining a pre-operative plan comprising pre-operative image data that includes a first portion of a patient bone and one or more reference fiducial markers;

obtaining post-operative image data that includes at least a second portion of the patient bone comprising a resected surface of the patient bone and the one or more fiducial markers;

co-registering the post-operative image data to the pre-operative image data based on a spatial position and orientation of the one or more reference fiducial markers relative to the first and second portion of the patient bone;

generating, based on the co-registration, an alignment image comprising a post-operative alignment of the resected surface with the patient bone;

determining, based on the alignment image, an accuracy measurement of the post-operative alignment with respect to the pre-operative plan.

14. The method of claim 13, further comprising measuring a resected bone fragment thickness and a saw blade thickness.

15. The method of claim 14, further comprising summing the resected bone fragment thickness and the saw blade thickness to determine a resection depth.

16. The method of claim 13, wherein co-registering the post-operative image data to the pre-operative image data comprises regression fitting the spatial position and orientation of the one or more fiducial markers in the pre-operative image data relative to the one or more fiducial markers in the post-operative image data.

17. The method of claim 13, further comprising defining one or more coordinate systems for the pre-operative image data.

18. The method of claim 17, wherein the one or more coordinate systems comprises a coordinate system for a femur of the patient and a coordinate system for a tibia of the patient.

19. The method of claim 13, wherein generating an alignment image comprises calculating a three-dimensional transformation based on the resected surface, the one or more coordinate systems, and the one or more reference fiducial markers.

20. A method of validating a surgical alignment, the method comprising:

obtaining pre-operative image data of a bone of a patient having a plurality of landmarks, wherein the pre-operative image data is aligned based on the bone of the patient;

obtaining post-operative image data of the bone of the patient;

establishing the plurality of landmarks in the post-operative image data;

co-registering the post-operative image data to one or more implant models based on the plurality of landmarks;

co-registering the post-operative image data to the pre-operative image data based on the plurality of landmarks;

comparing, based on the co-registration, a pre-operative plan to the post-operative image data; and determining, based on the comparison, an accuracy measurement of a post-operative alignment with respect to the pre-operative plan.

* * * * *